(12) United States Patent
Biggadike et al.

(10) Patent No.: US 6,878,698 B2
(45) Date of Patent: Apr. 12, 2005

(54) ANTI-INFLAMMATORY ANDROSTANE DERIVATIVES

(75) Inventors: Keith Biggadike, Stevenage (GB); Paul Spencer Jones, Stevenage (GB); Jeremy John Payne, Stevenage (GB)

(73) Assignee: Glaxo Group Limited, Greenford (GB)

(*) Notice: Subject to any disclaimer, the term of this patent is extended or adjusted under 35 U.S.C. 154(b) by 36 days.

(21) Appl. No.: 10/281,735

(22) Filed: Oct. 28, 2002

(65) Prior Publication Data

US 2003/0092690 A1 May 15, 2003

Related U.S. Application Data

(60) Division of application No. 10/066,961, filed on Feb. 4, 2002, now Pat. No. 6,537,983, which is a continuation-in-part of application No. PCT/GB01/03499, filed on Aug. 3, 2001.

(30) Foreign Application Priority Data

Apr. 7, 2001 (GB) .............................. 0108800

(51) Int. Cl.⁷ ......................... A61K 31/58; C07J 17/00; C07J 43/00
(52) U.S. Cl. ....................... 514/172; 540/108; 540/114
(58) Field of Search ......................... 514/172; 540/108, 540/114

(56) References Cited

U.S. PATENT DOCUMENTS

| | | | |
|---|---|---|---|
| 3,067,197 A | 12/1962 | Agnello et al. | |
| 3,639,434 A | 2/1972 | Oxley et al. | |
| 3,828,080 A | 8/1974 | May et al. | |
| 3,856,828 A | 12/1974 | Phillips et al. | |
| 3,981,894 A | 9/1976 | Phillips et al. | |
| 3,989,686 A | 11/1976 | Phillips et al. | |
| 4,093,721 A | 6/1978 | Phillips et al. | |
| 4,187,301 A | 2/1980 | Edwards | |
| 4,188,385 A | 2/1980 | Edwards | |
| 4,198,403 A | 4/1980 | Alvarez | |
| 4,261,984 A | 4/1981 | Alvarez | |
| 4,263,289 A | 4/1981 | Edwards | |
| 4,267,173 A | 5/1981 | Draper | |
| 4,285,937 A | 8/1981 | Kalvoda | |
| 4,310,466 A | 1/1982 | Edwards | |
| 4,335,121 A | 6/1982 | Phillipps et al. | |
| 4,377,575 A | 3/1983 | Phillips et al. | |
| 4,472,393 A | 9/1984 | Shapiro | |
| 4,607,028 A | 8/1986 | Schmidlin | |
| 4,710,495 A | 12/1987 | Bodor | |
| 4,861,765 A | 8/1989 | Mitsukuchi et al. | |
| 4,992,474 A | 2/1991 | Skidmore et al. | |
| 4,994,439 A | 2/1991 | Longenecker et al. | |
| 4,996,335 A | 2/1991 | Bodor | |
| 5,250,293 A | 10/1993 | Gleich | |
| 5,420,120 A | 5/1995 | Boltralik | |
| 5,658,549 A | 8/1997 | Akehurst et al. | |
| 5,707,984 A | 1/1998 | Tjoeng et al. | |
| 5,837,699 A | 11/1998 | Sequeira et al. | |
| 5,849,265 A | * 12/1998 | Li-Bovet et al. ............... 424/45 |
| 5,889,015 A | 3/1999 | Sequeira et al. | |
| 5,919,776 A | 7/1999 | Hagmann et al. | |
| 5,972,920 A | 10/1999 | Seidel | |
| 5,981,517 A | 11/1999 | Bodor | |
| 6,057,307 A | 5/2000 | Sequeira et al. | |

(Continued)

FOREIGN PATENT DOCUMENTS

| | | |
|---|---|---|
| DE | 2336693 | 2/1975 |
| DE | 2538569 | 3/1977 |
| EP | 0004773 | 10/1979 |
| EP | 0057401 | 8/1982 |
| EP | 00/57401 | 8/1982 |
| EP | 0135476 | 3/1985 |
| EP | 0179583 | 4/1986 |

(Continued)

OTHER PUBLICATIONS

Janette M. Mahoney et al., "Drug effects on the neovascularization to silver nitrate cauterization of the rat cornea" Current Eye Research, vol. 4, No. 5, 1985, pp. 531–535.

(Continued)

*Primary Examiner*—Barbara P. Badio
(74) *Attorney, Agent, or Firm*—James P. Riek

(57) ABSTRACT

According to one aspect of the invention, there is provided a pharmaceutical formulation for administration by inhalation comprising a compound of formula (I),

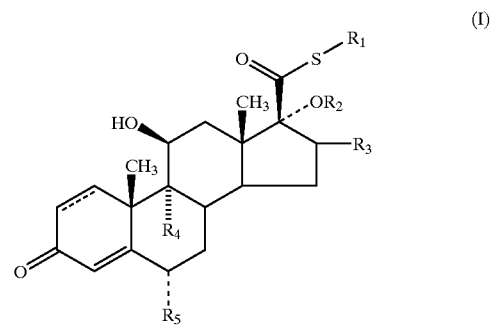

wherein
$R_1$ represents $C_{1-6}$ alkyl or $C_{1-6}$ haloalkyl;
$R_2$ represents —C(=O)-aryl or —C(=O)-heteroaryl;
$R_3$ represents hydrogen, methyl (which may be in either the α or β configuration) or methylene;
$R_4$ and $R_5$ are the same or different and each represents hydrogen or halogen; and
═══ represents a single or a double bond;
and salts and solvates thereof together with a long-acting $\beta_2$-adrenoreceptor agonist which formulation has a therapeutically useful effect in the treatment of COPD over a period of 24 hours or more.

141 Claims, No Drawings

U.S. PATENT DOCUMENTS

| | | | |
|---|---|---|---|
| 6,127,353 | A | 10/2000 | Yuen et al. |
| 6,136,294 | A | 10/2000 | Adjei et al. |
| 6,197,761 | B1 | 3/2001 | Biggadike et al. |
| 6,261,539 | B1 * | 7/2001 | Adjei et al. .................... 424/46 |
| 6,395,300 | B1 | 5/2002 | Straub et al. |
| 2002/0081266 | A1 | 6/2002 | Woolfe et al. |
| 2002/0103392 | A1 | 8/2002 | Stache et al. |
| 2002/0165211 | A1 | 11/2002 | Biggadike et al. |
| 2002/0173496 | A1 | 11/2002 | Biggadike |
| 2002/0177581 | A1 | 11/2002 | Biggadike |
| 2003/0073676 | A1 | 4/2003 | Biggadike et al. |
| 2003/0109511 | A1 | 6/2003 | Biggadike et al. |
| 2003/0144257 | A1 | 7/2003 | Biggadike et al. |
| 2003/0158163 | A1 | 8/2003 | Cuenoud et al. |

FOREIGN PATENT DOCUMENTS

| | | |
|---|---|---|
| EP | 0416951 | 3/1991 |
| EP | 0418716 | 3/1991 |
| EP | 0521455 | 1/1993 |
| EP | 0640616 | 3/1995 |
| EP | 0646593 | 4/1995 |
| FR | 580494 | 10/1986 |
| GB | 1384372 | 2/1975 |
| GB | 1438940 | 6/1976 |
| GB | 1517278 | 7/1978 |
| GB | 2079755 | 1/1982 |
| GB | 2140800 | 12/1984 |
| IL | 109656 | 2/1998 |
| JP | 04208267 | 7/1992 |
| WO | 92/14472 | 9/1992 |
| WO | 94/21229 | 9/1994 |
| WO | 95/31964 | 11/1995 |
| WO | 96/19199 | 6/1996 |
| WO | 97/05136 | 2/1997 |
| WO | 97/15298 | 5/1997 |
| WO | 97/24365 | 7/1997 |
| WO | 97/46243 | 12/1997 |
| WO | 98/17676 | 4/1998 |
| WO | 98/34596 | 8/1998 |
| WO | 98/43630 | 10/1998 |
| WO | 99/01467 | 1/1999 |
| WO | 99/25359 | 5/1999 |
| WO | 99/32089 | 7/1999 |
| WO | 00/16814 | 3/2000 |
| WO | 00/33892 | 6/2000 |
| WO | 00/38811 | 7/2000 |
| WO | 01/04118 | 1/2001 |
| WO | 01/15744 | 3/2001 |
| WO | 01/20331 | 3/2001 |
| WO | 01/54664 | 8/2001 |
| WO | 01/62722 | 8/2001 |
| WO | 01/78736 | 10/2001 |
| WO | 01/78739 | 10/2001 |
| WO | 01/78741 | 10/2001 |
| WO | 01/78745 | 10/2001 |
| WO | 02/00199 | 1/2002 |
| WO | 02/00679 | 1/2002 |
| WO | 02/007767 | 1/2002 |
| WO | 02/008243 | 1/2002 |
| WO | 0212265 | 2/2002 |
| WO | 0212266 | 2/2002 |
| WO | 02/013868 | 2/2002 |
| WO | 02/26723 | 4/2002 |
| WO | 02/053186 | 7/2002 |
| WO | 02066422 | 8/2002 |
| WO | 02070490 | 9/2002 |
| WO | 02076933 | 10/2002 |
| WO | 02/085296 | 10/2002 |
| WO | 02/088167 | 11/2002 |
| WO | 02/100879 | 12/2002 |
| WO | 03/013427 | 2/2003 |
| WO | 03/033000 | 4/2003 |
| WO | 03/035668 | 5/2003 |
| WO | 03/040691 | 5/2003 |
| WO | 03/042229 | 5/2003 |
| WO | 03/042230 | 5/2003 |
| ZA | 872389 | 4/1987 |

OTHER PUBLICATIONS

Richard A. Kenley et al., "An Automated, Column–Switching HPLC Method for Analyzing Active and Excipient Materials in Both Cream and Ointment Formulations," Drug Development and Industrial Pharmacy, vol. 11 (9&10), 1985, pp. 1781–1796.

R. Woodford et al., "Activity and bioavailability of a new steroid (Timobesone acetate) in cream and ointment compared with Lidex and Dermovate creams and ointments and Betnovate cream" Int'l Journal of Pharmaceutics, vol. 26 (1985) pp. 145–155.

Denis J. Kertesz et al., "Thiol Esters from Steroid 17β–Carboxylic Acids: Carboxylate Activation and Internal Participation by a 17α–Acylates" J. Org. Chem., vol. 51, 1986, pp. 2315–2328.

John T. H. Ong et al., "Micellar Solubilization of Timobesone Acetate in Aqueous and Aqueous Propylene Glycol Solutions of Ninionic Surfactants", Pharmaceutical Research, vol. 5, No. 11, 1988, pp. 704–708.

John T. H. Ong et al., Intrinsic Potencies of Novel Thiol Ester Corticosteroids RS–85095 and RS–21314 as Compared With Clobetasol 17–Propionate and Fluocinonide Arch Dermatol, vol. 125, Dec. 1989, pp. 1662–1665.

S.J. Lane et al., "Evaluation of a New Capillary Electrochromatography/Mass Spectrometry Interface Using Short Columns and High Field Strengths for Rapid and Efficient Analyses," Rapid Communications in Mass Spectrometry, vol. 10, 1996, pp. 733–736.

Franklin I. Aigbirthio et al., "Automated Radiosynthesis of No–carrier–added [S–fluoromethyl–$^{18}$F]Fluticasone Propionate as a Radiotracer for Lung Deposition Studies with PET" Journal of Labelled Compounds and Radiopharmaceuticals, vol. 39, No. 7, 1997, pp. 569–584.

Nisha Mistry et al., "Characterisation of impurities in bulk drug batches of fluticasone propionate using directly coupled HPLC–NMR spectroscopy and HPLC–MS," Journal of Pharmaceutical and Biomedical Analysis vol. 16, 1997, pp. 697–705.

Knobil, K., et al., "Adding Salmeterol Is More Effective Than Increasing The Dose Of Fluticasone For Patients With Asthma Who Are Symptomatic On Low Dose Fluticasone," European Respiratory review, Copenhagen, DK, vol. 12, No. SUPPL 29 Dec. 1998, pp. 19S–20S, XP000992769.

Nisha Mistry et al., Impurity profiling in bulk pharmaceutical batches uing 19F NMR spectroscopy and distinction between monomeric and dimeric impurities by NMR–based diffusion measurements, Journal of Pharmaceutical and Biomedical Analysis, vol. 19, 1999, pp. 511–517.

N. Smith et al., "Comparison of the electroosmotic flow profiles and selectivity of stationary phases used in capillary electrochromatography," Journal of Chormatography A., vol. 832, 1999, pp. 44–54.

R.C. Garner et al., "A validation study comparing accelerator MS and liquid scintillation counting for analysis of ¹⁴C–labelled drugs in plasma, urine and faecal extracts", Journal of Pharmaceutical and Biomedical Analysis vol. 24, 2000, pp. 197–209.

Harold S. Nelson et al. "Fluticasone propionate/salmeterol combination provides more effective asthma control than low–dose inhaled corticosteroid plus montelukast," J. Allergy Clin. Immunol., vol. 106, No. 6, Dec. 2000, pp. 1088–1095.

Gunnar Johansson et al., "Comparison of Salmeterol/Fluticasone Propionate Combination With Budesonide in Patients With Mild–to–Moderate Asthma" Clin. Drug Invest. vol. 21, No. 9, 2001, pp. 633–642.

Bertil Pettersson et al., Re–evaluation of the classical Mycoplasma lipophilum cluster (Weisburg et al. 1989) and description of two new clusters in the hominis group based on 16S rDNA sequences, Int'l Journal of Systematic & Evolutionary Microbiology (2001) vol. 51, pp. 633–643.

Sarah A. Lewis et al., "Association of specific allergen sensitization with socioeconomic factors and allergic disease in a population of Boston women", J. Allergy Clin. Immunol., vol. 107, No. 4, Apr. 2001, pp. 615–622.

Katherine A. Lyseng–Williamson et al., "Inhaled Salmeterol/Fluticasone Propionate Combination in Chronic Obstructive Pulmonary Disease," Am. J. Respir. Med. vol. 1, No. 4, 2002, pp. 273–282.

Jeffrey W. Millard et al., "Solubilization by cosolvents Establishing useful constants for the log–linear model," Int'l Journal of Pharmaceutics vol. 245, 2002, pp. 153–166.

C. Baumgarten et al., "Initial Treatment of Symptomatic Mild to Moderate Bronchial Asthma with the Salmeterol/Fluticasone Propionate (50/250µg) Combination Product (SAS 40023)" European Journal of Medical Research 2002, vol. 7, pp. 1–7.

Stephen J. Fowler et al., "Step–down therapy with low–dose fluticasone–salmeterol combination or medium–dose hydrofluoroalkane 134a–beclomethasone alone" J. Allergy Clin. Immunol., vol. 109, No. 6, Jun. 2002, pp. 929–935.

Elizabeth F. Juniper et al., "Impact of Inhaled Salmeterol/Fluticasone Propionate Combination Product versus Budesonide on the Health–Related Quality of Life of Patients with Asthma," Am. J. Respir. Med., vol. 1, No. 6, 2002, pp. 435–440.

William Busse et al., "Steroid–sparing effects of fluticasone propionate 100 µg and salmeterol 50 µg administered twice daily in a single product in patients previously controlled with fluticasone propionate 250 µg administered twice daily" J. Allergy Clin. Immunol., vol. 111, No. 1, Jan. 2003, pp. 57–65.

Ueno H et al, "Synthesis and Evaluation of Antiinflammatory Activities of a Series of Corticosteroid 17.Alpha–Esters Containing a Functional Group", Journal of Medicinal Chemistry, American Chemical Society, vol. 34, No. 8, Aug. 1991, pp. 2468–2473.

Peter J Barnes, "Novel approaches and targets for treatment of Chronic Obstructive Pulmonary Disease" American Journal of Respiratory and Critical Care Medicine, vol. 160, 1999, pp. S72–S79.

B.J O Conner; "Combination Therapy", Pulmonary Pharmacology and Therapeutics, vol. 11, No. 5/6, 1998, pp. 397 399.

Peter J Barnes, "Chronic Obstructive Pulmonary Disease: new opportunities for drug development" Trends in Pharmacological Sciences, Elsevenir Trends Journal, vol. 19, No. 10, 1998, pp. 415 –423.

Simon Bowler, "Long acting beta agonists", Australian Family Physician, vol. 27, No. 12, 1998, pp. 1114–1118.

Naedle–Risha R et al, "Dual components of optimal asthma therapy: scientific and clinical rationale for the use of long acting beta–agonists with inhaled corticosteroids", The Journal of the American Osteopathic Association, vol. 101, No. 9, Sep. 2001, pp. 2001–2009.

T Van Der Molen et al., "Effects of the Long Acting Beta Agonist Formoterol on Asthma Control in Asthmatic Patients Using Inhaled Corticosteroids"; vol. 52, No. 6, 1997, pp. 535–539.

B.N. Lutsky et al, "A Novel Class of potent Topical Antiinflammatory Agents: 17 Benzoylated, 7—Halogeno Substituted Corticosteroids", Arzeneimittel Forschung, vol. 29, No. 11, Nov. 1979, pp. 1662–1667.

Peter J. Barnes, "Efficacy of Inhaled Corticosteroids in Asthma", The Journal of Allergy and Clinical Immunology, vol. 102, No. 4, pp. 531–538.

U.S. Appl. No. 09/958,050, filed on Oct. 2, 2001.

U.S. Appl. No. 10/066,836, filed on Feb. 4, 2002.

U.S. Appl. No. 10/066,951, filed on Feb. 4, 2002.

U.S. Appl. No. 10/066,964, filed on Feb. 4, 2002.

U.S. Appl. No. 10/067,010, filed on Feb. 4, 2002.

U.S. Appl. No. 10/067,020, filed on Feb. 4, 2002.

U.S. Appl. No. 10/200,364, filed on Jul. 22, 2002.

U.S. Appl. No. 10/241,658, filed on Sep. 11, 2002.

Phillips, G.H., et al., "Synthesis and Structure–Activity Relationships in a series of Antiinflammatory Corticosteroid Analogues, Halomethyl Androstane–17β–carbothioates and– 17β–carboselenoates," Journal of Medicinal Chemistry 1994, 37, 3717–3729.

Isogai, Mitsutaka, et. al., "Binding Affinities of Mometasone Furoate and Related Compounds Including its Metabolites for the Glucocorticoid receptor of Rat Skin Tissue", J. Steroid Biochem. Mol. Biol. 1993, 44, 141–145.

Popper, T.L., et al., "Structure—Activity Relationship of a Series of Novel Topical Corticosteroids", Journal of Steroid Biochemistry 1987, 27, 837–843, 840–841.

Shapiro, E.L., et. al., " 17 Heteroaroyl Esters of Corticosteroids 2. 11–Beta Hydroxy Series", Journal of Medicinal Chemistry 1987, 30, 1581–1588.

* cited by examiner

ANTI-INFLAMMATORY ANDROSTANE DERIVATIVES

This is a divisional application of U.S. Ser. No. 10/066,961, filed 4 Feb. 2002, now U.S. Pat. No. 6,537,983 which is a Continuation-in-part of International Patent Application Serial No. PCT.GB01.03499 filed 3 Aug. 2001, based upon United Kingdom Patent Application No. GB0108800.4 filed 7 Apr. 2001.

The present invention relates to novel anti-inflammatory and anti-allergic compounds of the androstane series and to processes for their preparation. The present invention also relates to pharmaceutical formulations containing the compounds and to therapeutic uses thereof, particularly for the treatment of inflammatory and allergic conditions.

Glucocorticoids which have anti-inflammatory properties are known and are widely used for the treatment of inflammatory disorders or diseases such as asthma and rhinitis. For example, U.S. Pat. No. 4,335,121 discloses 6α,9α-Difluoro-17α-(1-oxopropoxy)-11β-hydroxy-16α-methyl-3-oxo-androsta-1,4-diene-17β-carbothioic acid S-fluoromethyl ester (known by the generic name of fluticasone propionate) and derivatives thereof. The use of glucocorticoids generally, and especially in children, has been limited in some quarters by concerns over potential side effects. The side effects that are feared with glucocorticoids include suppression of the Hypothalamic-Pituitary-Adrenal (HPA) axis, effects on bone growth in children and on bone density in the elderly, ocular complications (cataract formation and glaucoma) and skin atrophy. Certain glucocorticoid compounds also have complex paths of metabolism wherein the production of active metabolites may make the pharmacodynamics and pharmacokinetics of such compounds difficult to understand. Whilst the modern steroids are very much safer than those originally introduced it remains an object of research to produce new molecules which have excellent anti-inflammatory properties, with predictable pharmacokinetic and pharmacodynamic properties, with an attractive side effect profile, and with a convenient treatment regime.

We have identified a novel series of glucocorticoids, which substantially meets these objectives.

Thus, according to one aspect of the invention, there is provided a compound of formula (I)

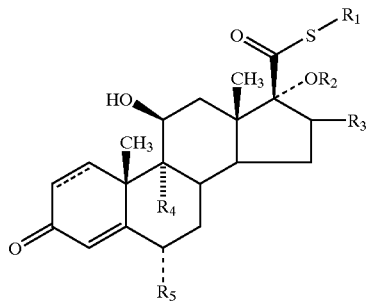

(I)

wherein
R$_1$ represents C$_{1-6}$ alkyl or C$_{1-6}$ haloalkyl;
R$_2$ represents —C(=O)-aryl or —C(=O)-heteroaryl;
R$_3$ represents hydrogen, methyl (which may be in either the α or β configuration) or methylene;
R$_4$ and R$_5$ are the same or different and each represents hydrogen or halogen; and
=== represents a single or a double bond;
and salts and solvates thereof.

References to the term "aryl" include references to phenyl which may be optionally substituted with one or more substituents.

References to the term "heteroaryl" include references to 5 or 6 membered heterocyclic aromatic rings containing 1–3 hetero atoms selected from N, O and S (e.g. pyridinyl, pyrimidinyl, thienyl (eg thien-2-yl or thien-3-yl), furanyl (eg furan-2-yl or furan-3-y), pyrrolyl (eg 1H-pyrrol-2-yl), oxazolyl, thiadiazolyl (eg 1,2,3-thiadiazol-5-yl, 1,2,5-thiadiazol-3-yl or 1,2,3-thiadiazol-4-yl)). In one respect the heterocycle is preferably thiophenyl, pyrrolyl or furanyl, more preferably thiophenyl or furanyl. Further examples include thiazolyl (eg 1,3-thiazolyl-5-yl or 1,3-thiazolyl-4-yl), isoxazolyl (eg isoxazol-5-yl or isoxazol-4-yl), isothiazolyl (eg isothiazol-3-yl or isothiazol-5-yl), pyrazolyl (eg 1H-pyrazol-5-yl) and imidazolyl (eg 1H-imidazol-5-yl).

All of the previously named heterocycles may be optionally substituted with one or more (e.g. 1 or 2) substituents.

Examples of substituents for aryl and heteroaryl include C$_{1-6}$ alkyl (e.g. methyl) or halogen (e.g. chlorine or bromine). Other examples include C$_{1-6}$alkoxy (e.g. methoxy or ethoxy).

Examples of substituted furanyl include 3-Me-furan-2-yl, 5-Br-furan-2-yl, 2-Me-furan-3-yl and 2,5-diMe-furan-3-yl. Examples of substituted thienyl include 3-Me-thien-2-yl, 5-Me-thien-2-yl, 5-Cl-thien-2-yl, 3-Cl-thien-2-yl, 3-Br-thien-2-yl, 3-Ethoxy-thien-2-yl, 4-methoxy-thien-3-yl, 2,5-diCl-thien-3-yl and 4-methoxy-5-Cl-thien-3-yl. Examples of substituted pyrrolyl include 1-Me-1H-pyrrol-2-yl. Examples of substituted thiazolyl include 4-Me-1,3-thiazol-5-yl, 2,4-diMe-1,3-thiazol-5-yl and 2-Me-1,3-thiazol-4-yl. Examples of substituted thiadiazolyl include 4-Me-1,2,3-thiadiazol-5-yl. Examples of substituted isoxazolyl include 3-Me-isoxazol-5-yl, 5-Me-isoxazol-3-yl, 5-Me-isoxazol-4-yl and 3,5-diMe-isoxazol-4-yl. Examples of substituted pyrazolyl include 1,3-diMe-1H-pyrazol-5-yl and 1-Et-3-Me-1H-pyrazol-5-yl. Examples of substituted imidazolyl include 1-Me-1H-imidazol-5-yl.

Examples of solvates include hydrates.

Examples of salts of compounds of formula (I) include physiologically acceptable salts which may be formed with basic compounds (such as when heteroaryl is basic) eg. acetate, benzoate, citrate, succinate, lactate, tartrate, fumarate and maleate.

References hereinafter to a compound according to the invention includes both compounds of formula (I) and salts and solvates thereof, particularly pharmaceutically acceptable salts and solvates.

It will be appreciated that the invention includes within its scope all stereoisomers of the compounds of formula (I) and mixtures thereof.

Preferably, the absolute stereochemistry will be as shown in the representation of compounds of formula (I).

Examples of C$_{1-6}$ haloalkyl that R$_1$ may represent include C$_{1-6}$ alkyl substituted by 1–3 halogen atoms, preferably 1 halogen atom. Preferred halogen atoms are selected from bromine, chlorine and fluorine. Examples of C$_{1-6}$ alkyl that R$_1$ may represent include methyl.

We prefer R$_1$ to represent fluoromethyl, chloromethyl, bromomethyl or 2'-fluoroethyl, especially fluoromethyl.

We prefer R$_2$ to represent —C(=O)-heteroaryl. Preferably the heteroaryl is a 5-membered heterocyclic aromatic ring containing 1 to 3 heteroatoms selected from O, N and S which may optionally be substituted. In one respect, preferably heteroaryl represents furanyl, pyrrolyl or thiophenyl, more preferably furanyl or thiophenyl eg 2-furanyl, 3-furanyl, 2-thiophenyl or 3-thiophenyl, especially furanyl, particularly 2-furanyl. However it may also be preferred that heteroaryl represents pyrrolyl or thiophenyl, more preferably thiophenyl eg 2-thiophenyl or 3-thiophenyl which pyrrolyl or thiophenyl may be optionally substituted.

Of particular interest are compounds in which the heteroaryl is a 5-membered heterocyclic aromatic ring containing 2 heteroatoms selected from O, N and S. Thus a further set of preferred compounds is that in which $R_2$ represents optionally substituted thiazolyl. A further set of preferred compounds is that in which $R_2$ represents optionally substituted isothiazolyl. A further set of preferred compounds is that in which $R_2$ represents optionally substituted pyrazolyl. A further set of preferred compounds is that in which $R_2$ represents optionally substituted isoxazolyl. A further set of preferred compounds is that in which $R_2$ represents optionally substituted isothiazolyl. A further set of preferred compounds is that in which $R_2$ represents optionally substituted imidazolyl.

Of particular interest is compounds in which the heteraryl is a 5-membered heterocyclic aromatic ring containing 3 heteroatoms selected from O, N and S. Thus a further set of preferred compounds is that in which $R_2$ represents optionally substituted thiadiazolyl.

Compounds in which $R_2$ represents —C(=O)-aryl (preferably aryl represents phenyl) are also of particular interest.

We prefer $R_3$ to represent methyl, especially methyl in the α configuration. Compounds in which $R_3$ represents methyl in the β configuration are also of particular interest.

Compounds of formula (I) in which $R_4$ and $R_5$, which can be the same or different, each represents hydrogen, fluorine or chlorine, particularly hydrogen or fluorine, are preferred. Especially preferred are compounds in which both $R_4$ and $R_5$ are fluorine.

Preferably,

----- represents a double bond. Compounds in which

----- represents a single bond are also of particular interest.

A particularly preferred group of compounds of the present invention are compounds of formula (I) in which $R_1$ is fluoromethyl; $R_2$ is —C(=O)-2-furanyl; $R_3$ is methyl; $R_4$ and $R_5$, which can be the same or different, each represents hydrogen or fluorine, especially fluorine, and

----- represents a single or a double bond.

It is to be understood that the present invention covers all combinations of particularly and preferred groups referred to hereinabove.

Preferred compounds of formula (I) include:

6α,9α-Difluoro-17α-[(2-furanylcarbonyl)oxy]-11β-hydroxy-16α-methyl-3-oxo-androsta-1,4-diene-17β-carbothioic acid S-fluoromethyl ester;

6α,9α-Difluoro-17β-[(3-furanylcarbonyl)oxy]-11β-hydroxy-16α-methyl-3-oxo-androsta-1,4-diene-17β-carbothioic acid S-fluoromethyl ester;

6α,9α-Difluoro-11β-hydroxy-16α-methyl-3-oxo-17α-[(2-thienylcarbonyl)oxy]-androsta-1,4-diene-17β-carbothioic acid S-fluoromethyl ester;

6α,9α-Difluoro-11β-hydroxy-16α-methyl-3-oxo-17α-[(3-thienylcarbonyl)oxy]-androsta-1,4-diene-17β-carbothioic acid S-fluoromethyl ester;

17α-(Benzoyl)oxy-6α,9α-Difluoro-11β-hydroxy-16α-methyl-3-oxo-androsta-1,4-diene-17β-carbothioic acid S-fluoromethyl ester;

9α-Fluoro-17α-[(2-furanylcarbonyl)oxy]-11β-hydroxy-16β-methyl-3-oxo-androsta-1,4-diene-17β-carbothioic acid S-fluoromethyl ester; and 6α,9α-Difluoro-17α-[(2-furanylcarbonyl)oxy]-11β-hydroxy-16α-methyl-3-oxo-androst-4-ene-17β-carbothioic acid S-fluoromethyl ester or a salt or solvate thereof.

Particularly preferred compounds of formula (I) include:

6α,9α-Difluoro-17α-[(2-furanylcarbonyl)oxy]-11β-hydroxy-16α-methyl-3-oxo-androsta-1,4-diene-17β-carbothioic acid S-fluoromethyl ester;

6α,9α-Difluoro-17α-[(3-furanylcarbonyl)oxy]-11β-hydroxy-16α-methyl-3-oxo-androsta-1,4-diene-17β-carbothioic acid S-fluoromethyl ester;

6α,9α-Difluoro-11β-hydroxy-16α-methyl-3-oxo-17α-[(2-thienylcarbonyl)oxy]-androsta-1,4-diene-17β-carbothioic acid S-fluoromethyl ester;

6α,9α-Difluoro-11β-hydroxy-16α-methyl-3-oxo-17α-[(3-thienylcarbonyl)oxy]-androsta-1,4-diene-17β-carbothioic acid S-fluoromethyl ester;

6α,9α-Difluoro-17α-[(2-furanylcarbonyl)oxy]-11β-hydroxy-16α-methyl-3-oxo-androst-4-ene-17β-carbothioic acid S-fluoromethyl ester or a salt or solvate thereof.

The compounds named as Examples 8–43 are also of particular interest, especially Examples 8–22 and 24–43, most especially examples 8–9, 11–13, 15–22 and 24–43.

The compounds of formula (I) have potentially beneficial anti-inflammatory or anti-allergic effects, particularly upon topical administration, demonstrated by, for example, their ability to bind to the glucocorticoid receptor and to illicit a response via that receptor with long lasting effect. Hence, the compounds of formula (I) are useful in the treatment of inflammatory and/or allergic disorders, especially in once-per-day therapy.

Compounds of formula (I) are predicted to undergo highly efficient hepatic metabolism to yield the corresponding 17-β carboxylic acid (X) in which $R_2$–$R_4$ and

----- are as defined above as the sole major metabolite in rat and human in vitro systems. We have established that this is the case for Example 1 and metabolite (X) for Example 1 has been synthesised and demonstrated to be >1000 fold less active than the parent compound in in vitro functional glucocorticoid agonist assays. Analogues of (X) wherein $R_2$ represents a group other than 2-furanylcarbonyl are expected also to have very low activity.

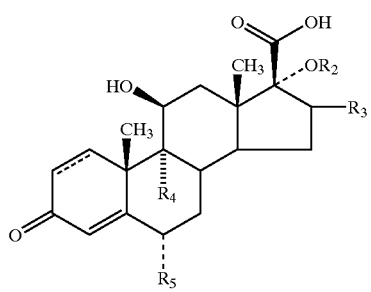

(X)

This efficient hepatic metabolism is reflected by in vivo data in the rat for certain examples, which have demonstrated plasma clearance at a rate approaching hepatic blood flow (Examples 1, 4, 19, 24, 25 and 28) and an oral bioavailability of <1%, consistent with extensive first-pass metabolism (Example 1).

In vitro metabolism studies in human hepatocytes have demonstrated that Example 1 is metabolised in an identical manner to fluticasone propionate but that conversion of Example 1 to the inactive acid metabolite occurs approximately 5-fold more rapidly than with fluticasone propionate. This very efficient hepatic inactivation would be expected to minimise systemic exposure in man leading to an improved safety profile.

Inhaled steroids are also absorbed through the lung and this route of absorption makes a significant contribution to systemic exposure. Reduced lung absorption could therefore provide an improved safety profile. Studies with Example 1 have shown significantly lower exposure to Example 1 than with fluticasone propionate after dry powder delivery to the lungs of anaesthetised pigs.

An improved safety profile is believed to allow the compounds of formula (I) to demonstrate the desired anti-inflammatory effects when administered once-per day. Once-per-day dosing is considered to be significantly more convenient to patients than the twice-per day dosing regime that is normally employed for fluticasone propionate.

Examples of disease states in which the compounds of the invention have utility include skin diseases such as eczema, psoriasis, allergic dermatitis neurodermatitis, pruritis and hypersensitivity reactions; inflammatory conditions of the nose, throat or lungs such as asthma (including allergen-induced asthmatic reactions), rhinitis (including hayfever), nasal polyps, chronic obstructive pulmonary disease, interstitial lung disease, and fibrosis; inflammatory bowel conditions such as ulcerative colitis and Crohn's disease; and auto-immune diseases such as rheumatoid arthritis.

Compounds of the invention may also have use in the treatment of conjunctiva and conjunctivitis.

It will be appreciated by those skilled in the art that reference herein to treatment extends to prophylaxis as well as the treatment of established conditions.

As mentioned above, compounds of formula (I) are useful in human or veterinary medicine, in particular as anti-inflammatory and anti-allergic agents.

There is thus provided as a further aspect of the invention a compound of formula (I) or a physiologically acceptable salt or solvate thereof for use in human or veterinary medicine, particularly in the treatment of patients with inflammatory and/or allergic conditions, especially for treatment once-per-day.

According to another aspect of the invention, there is provided the use of a compound of formula (I) or physiologically acceptable salt or solvate thereof for the manufacture of a medicament for the treatment of patients with inflammatory and/or allergic condition, especially for treatment once-per-day.

In a further or alternative aspect, there is provided a method for the treatment of a human or animal subject with an inflammatory and/or allergic condition, which method comprises administering to said human or animal subject an effective amount of a compound of formula (I) or physiologically acceptable salt or solvate thereof, especially for administration once-per-day.

The compounds according to the invention may be formulated for administration in any convenient way, and the invention therefore also includes within its scope pharmaceutical compositions comprising a compound of formula (I) or physiologically acceptable salt or solvate thereof together, if desirable, in admixture with one or more physiologically acceptable diluents or carriers. Pharmaceutical compositions suitable for once-per-day administration are of particular interest.

Further, there is provided a process for the preparation of such pharmaceutical compositions which comprises mixing the ingredients.

The compounds according to the invention may, for example, be formulated for oral, buccal, sublingual, parenteral, local or rectal administration, especially local administration.

Local administration as used herein, includes administration by insufflation and inhalation. Examples of various types of preparation for local administration include ointments, lotions, creams, gels, foams, preparations for delivery by transdermal patches, powders, sprays, aerosols, capsules or cartridges for use in an inhaler or insufflator or drops (e.g. eye or nose drops), solutions/suspensions formebulisation, suppositories, pessaries, retention enemas and chewable or suckable tablets or pellets (e.g. for the treatment of aphthous ulcers) or liposome or microencapsulation preparations.

Advantageously compositions for topical administration to the lung include dry powder compositions and spray compositions.

Dry powder compositions for topical delivery to the lung may, for example, be presented in capsules and cartridges for use in an inhaler or insufflator of, for example, gelatine. Formulations generally contain a powder mix for inhalation of the compound of the invention and a suitable powder base such as lactose or starch. Use of lactose is preferred. Each capsule or cartridge may generally contain between 20 µg–10 mg of the compound of formula (I) optionally in combination with another therapeutically active ingredient. Alternatively, the compound of the invention may be presented without excipients. Packaging of the formulation may be suitable for unit dose or multi-dose delivery. In the case of multi-dose delivery, the formulation can be pre-metered (eg. as in Diskus, see GB 2242134 or Diskhaler, see GB 2178965, 2129691 and 2169265) or metered in use (eg. as in Turbuhaler, see EP 69715). An example of a unit-dose device is Rotahaler (see GB 2064336). The Diskus inhalation device comprises an elongate strip formed from a base sheet having a plurality of recesses spaced along its length and a lid sheet hermetically but peelably sealed thereto to define a plurality of containers, each container having therein an inhalable formulation containing a compound of formula (I) optionally in combination with another therapeutically active ingredient preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

Spray compositions may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the compound of formula (I) optionally in combination with another therapeutically active ingredient and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants e.g. oleic acid or lecithin and cosolvents e.g. ethanol. One example formulation is excipient free and consists essentially of (eg consists of) a compound of formula (I) (optionally together with another active ingredient) and a propellant selected from 1,1,1,2-tetrafluoroethane, 1,1,1,2,3,3,3-heptafluoro-n-propane and mixture thereof. Another example formulation comprises particulate compound of formula (I), a propellant selected from 1,1,1,2-tetrafluoroethane, 1,1,1,2,3,3,3-heptafluoro-n-propane and mixture thereof and a suspending agent which is soluble in the propellant eg an oligolactic acid or derivative thereof as described in WO94/21229. The preferred propellant is 1,1,1,2-tetrafluoroethane. Pressurised formulations will generally be retained in a canister (eg an aluminium canister) closed with a valve (eg a metering valve) and fitted into an actuator provided with a mouthpiece.

Medicaments for administration by inhalation desirably have a controlled particle size. The optimum particle size for inhalation into the bronchial system is usually 1–10 $\mu$m, preferably 2–5 $\mu$m. Particles having a size above 20 $\mu$m are generally too large when inhaled to reach the small airways. To achieve these particle sizes the particles of compound of formula (I) (and any further therapeutically active ingredient) as produced may be size reduced by conventional means eg. by micronisation. The desired fraction may be separated out by air classification or sieving. Preferably, the particles will be crystalline, prepared for example by a process which comprises mixing in a continuous flow cell in the presence of ultrasonic radiation a flowing solution of compound of formula (I) as medicament in a liquid solvent with a flowing liquid antisolvent for said medicament (eg as described in International Patent Application PCT/GB99/04368) or else by a process which comprises admitting a stream of solution of the substance in a liquid solvent and a stream of liquid antisolvent for said substance tangentially into a cylindrical mixing chamber having an axial outlet port such that said streams are thereby intimately mixed through formation of a vortex and precipitation of crystalline particles of the substance is thereby caused (eg as described in International Patent Application PCT/GB00/04327). When an excipient such as lactose is employed, generally, the particle size of the excipient will be much greater than the inhaled medicament within the present invention. When the excipient is lactose it will typically be present as milled lactose, wherein not more than 85% of lactose particles will have a MMD of 60–90 $\mu$m and not less than 15% will have a MMD of less than 15 $\mu$m.

Formulations for administration topically to the nose include pressurised aerosol formulations and aqueous formulations administered to the nose by pressurised pump.

Aqueous formulations for administration to the lung or nose may be provided with conventional excipients such as buffering agents, tonicity modifying agents and the like. Aqueous formulations may also be administered to the nose by nebulisation.

Other possible presentations include the following:

Ointments, creams and gels, may, for example, be formulated with an aqueous or oily base with the addition of suitable thickening and/or gelling agent and/or solvents. Such bases may thus, for example, include water and/oran oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

If appropriate, the formulations of the invention may be buffered by the addition of suitable buffering agents.

The proportion of the active compound of formula (I) in the local compositions according to the invention depends on the precise type of formulation to be prepared but will generally be within the range of from 0.001 to 10% by weight. Generally, however for most types of preparations advantageously the proportion used will be within the range of from 0.005 to 1% and preferably 0.01 to 0.5%. However, in powders for inhalation or insufflation the proportion used will usually be within the range of from 0.1 to 5%.

Aerosol formulations are preferably arranged so that each metered dose or "puff" of aerosol contains 1 $\mu$g–2000 $\mu$g eg 20 $\mu$g–2000 $\mu$g, preferably about 20 $\mu$g–500 $\mu$g of a compound of formula (I) optionally in combination with another therapeutically active ingredient. Administration may be once daily or several times daily, for example 2, 3, 4 or 8 times, giving for example 1, 2 or 3 doses each time. Preferably the compound of formula (I) is delivered once or twice daily, especially once per day. The overall daily dose with an aerosol will typically be within the range 10 $\mu$g–10 mg eg 100 $\mu$g–10 mg preferably, 200 $\mu$g–2000 $\mu$g.

Since the compounds of formula (I) are long-acting, preferably the compound will be delivered once-per-day and the dose will be selected so that the compound has a therapeutic effect in the treatment of respiratory disorders (eg asthma or COPD, particularly asthma) over 24 hours or more.

Topical preparations may be administered by one or more applications per day to the affected area; over skin areas occlusive dressings may advantageously be used. Continuous or prolonged delivery may be achieved by an adhesive reservoir system.

For internal administration the compounds according to the invention may, for example, be formulated in conventional manner for oral, parenteral or rectal administration. Formulations for oral administration include syrups, elixirs, powders, granules, tablets and capsules which typically contain conventional excipients such as binding agents, fillers, lubricants, disintegrants, wetting agents, suspending agents, emulsifying agents, preservatives, buffer salts, flavouring, colouring and/or sweetening agents as appropriate. Dosage unit forms are, however, preferred as described below.

Preferred forms of preparation for internal administration are dosage unit forms i.e. tablets and capsules. Such dosage unit forms contain from 0.1 mg to 20 mg preferably from 2.5 to 10 mg of the compounds of the invention.

The compounds according to the invention may in general may be given by internal administration in cases where systemic adreno-cortical therapy is indicated.

In general terms preparations, for internal administration may contain from 0.05 to 10% of the active ingredient dependent upon the type of preparation involved. The daily dose may vary from 0.1 mg to 60 mg, e.g. 5–30 mg, dependent on the condition being treated, and the duration of treatment desired.

Slow release or enteric coated formulations may be advantageous, particularly for the treatment of inflammatory bowel disorders.

The pharmaceutical compositions according to the invention may also be used in combination with another therapeutically active agent, for example, a $\beta_2$ adrenoreceptor agonist, an anti-histamine or an anti-allergic. The invention thus provides, in a further aspect, a combination comprising a compound of formula (I) or a physiologically acceptable salt or solvate thereof together with another therapeutically active agent, for example, a $\beta_2$-adrenoreceptor agonist, an anti-histamine or an anti-allergic.

Examples of $\beta_2$-adrenoreceptor agonists include salmeterol (eg as racemate or a single enantiomer such as the R-enantiomer), salbutamol, formoterol, salmefamol, fenoterol or terbutaline and salts thereof, for example the xinafoate salt of salmeterol, the sulphate salt or free base of salbutamol or the fumarate salt of formoterol. Pharmaceutical compositions employing combinations with long-acting $\beta_2$-adrenoreceptor agonists (eg salmeterol and salts thereof) are particularly preferred, especially those which have a therapeutic effect (eg in the treatment of asthma or COPD, particularly asthma) over 24 hours or more.

Since the compound of formula (I) is long-acting, preferably the composition comprising the compound of formula (I) and the long-acting $\beta_2$-adrenoreceptor agonists will be delivered once-per-day and the dose of each will be selected so that the composition has a therapeutic effect in the treatment of respiratory disorders effect (eg in the treatment of asthma or COPD, particularly asthma) over 24 hours or more.

Examples of anti-histamines include methapyrilene or loratadine.

Other suitable combinations include, for example, other anti-inflammatory agents eg. NSAIDs (eg. sodium cromoglycate, nedocromil sodium, PDE4 inhibitors, leukotriene antagonists, iNOS inhibitors, tryptase and elastase inhibitors, beta-2 integrin antagonists and adenosine 2a agonists)) or antiinfective agents (eg. antibiotics, antivirals).

Of particular interest is use of the compounds of formula (I) in combination with a phosphodiesterase 4 (PDE4) inhibitor. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family as well as PDE4. Generally it is preferred to use a PDE4 inhibitor which has an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity. For the purposes of this disclosure, the cAMP catalytic site which binds R and S rolipram with a low affinity is denominated the "low affinity" binding site (LPDE 4) and the other form of this catalytic site which binds rolipram with a high affinity is denominated the "high affinity" binding site (HPDE 4). This term "HPDE4" should not be confused with the term "hPDE4" which is used to denote human PDE4. Initial experiments were conducted to establish and validate a [$^3$H]-rolipram binding assay. Details of this work are given in the Binding Assays described in detail below.

The preferred PDE4 inhibitors of use in this invention will be those compounds which have a salutary therapeutic ratio, i.e., compounds which preferentially inhibit cAMP catalytic activity where the enzyme is in the form that binds rolipram with a low affinity, thereby reducing the side effects which apparently are linked to inhibiting the form which binds rolipram with a high affinity. Another way to state this is that the preferred compounds will have an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity.

A further refinement of this standard is that of one wherein the PDE4 inhibitor has an $IC_{50}$ ratio of about 0.1 or greater; said ratio is the ratio of the $IC_{50}$ value for competing with the binding of 1 nM of [$^3$H]R-rolipram to a form of PDE4 which binds rolipram with a high affinity over the $IC_{50}$ value for inhibiting the PDE4 catalytic activity of a form which binds rolipram with a low affinity using 1 $\mu$M[$^3$H]-cAMP as the substrate.

Examples of useful PDE4 inhibitors are:
(R)-(+)-1-(4-bromobenzyl)-4-[(3-cyclopentyloxy)-4-methoxyphenyl]-2-pyrrolidone;
(R)-(+)-1-(4-bromobenzyl)-4-[(3-cyclopentyloxy)-4-methoxyphenyl]-2-pyrrolidone;
3-(cyclopentyloxy-4-methoxyphenyl)-1-(4-N'-[N2-cyano-S-methyl-isothioureido]benzyl)-2-pyrrolidone;
cis 4-cyano-4-(3-cyclopentyloxy-4-methoxyphenyl) cyclohexan-1-carboxylic acid];
cis-[4-cyano-4-(3-cyclopropylmethoxy-4-difluoromethoxyphenyl)cyclohexan-1-ol];
(R)-(+)-ethyl[4-(3-cyclopentyloxy-4-methoxyphenyl) pyrrolidine-2-ylidene]acetate; and
(S)-(−)-ethyl[4-(3-cyclopentyloxy-4-methoxyphenyl) pyrrolidine-2-ylidene]acetate.

Most preferred are those PDE4 inhibitors which have an $IC_{50}$ ratio of greater than 0.5, and particularly those compounds having a ratio of greater than 1.0. Preferred compounds are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl) cyclohexan-1-ol]; these are examples of compounds which bind preferentially to the low affinity binding site and which have an $IC_{50}$ ratio of 0.1 or greater.

Other compounds of interest include:
Compounds set out in U.S. Pat. No. 5,552,438 issued 3 Sep. 1996; this patent and the compounds it discloses are incorporated herein in full by reference. The compound of particular interest, which is disclosed in U.S. Pat. No. 5,552,438, is cis-4-cyano-4-[3-(cyclopentyloxy)-4-methoxyphenyl]cyclohexane-1-carboxylic acid (also known as cilomalast) and its salts, esters, pro-drugs or physical forms;
AWD-12-281 from Astra (Hofgen, N. et al. 15th EFMC Int Symp Med Chem (Sept 6–10, Edinburgh) 1998, Abst P. 98); a 9-benzyladenine derivative nominated NCS-613 (INSERM); D-4418 from Chiroscience and Schering-Plough; a benzodiazepine PDE4 inhibitor identified as CI-1018 (PD-168787; Parke-Davis/Warner-Lambert); a benzodioxole derivative Kyowa Hakko disclosed in WO 9916766; V-11294A from Napp (Landells, L. J. et al. Eur Resp J [Annu Cong Eur Resp Soc (Sept 19–23, Geneva) 1998] 1998, 12(Suppl. 28): Abst P2393); roflumilast (CAS reference No 162401-32-3) and a pthalazinone (WO 9947505) from Byk-Gulden; or a compound identified as T-440 (Tanabe Seiyaku; Fuji, K. et al. J Pharmacol Exp Ther, 1998, 284(1): 162).

Phosphodiesterase and Rolipram Binding Assays

Assay Method 1A

Isolated human monocyte PDE4 and hrPDE (human recombinant PDE4) was determined to exist primarily in the low affinity form. Hence, the activity of test compounds against the low affinity form of PDE4 can be assessed using standard assays for PDE4 catalytic activity employing 1 μM [$^3$H]cAMP as a substrate (Torphy et al., J. of Biol. Chem., Vol. 267, No. 3 pp1798–1804, 1992).

Rat brain high speed supernatants were used as a source of protein and both enantiomers of [$^3$H]-rolipram were prepared to a specific activity of 25.6 Ci/mmol. Standard assay conditions were modified from the published procedure to be identical to the PDE assay conditions, except for the last of the cAMP: 50 mM Tris HCl (pH 7.5), 5 mM MgCl$_2$, 50 μM 5'-AMP and 1 nM of [$^3$H]-rolipram (Torphy et al., J. of Biol. Chem., Vol. 267, No. 3 pp1798–1804, 1992). The assay was run for 1 hour at 30° C. The reaction was terminated and bound ligand was separated from free ligand using a Brandel cell harvester. Competition for the high affinity binding site was assessed under conditions that were identical to those used for measuring low affinity PDE activity, expect that [$^3$H]-cAMP was not present.

Assay Method 1B

Measurement of Phosphodiesterase Activity

PDE activity was assayed using a [$^3$H]cAMP SPA or [$^3$H]cGMP SPA enzyme assay as described by the supplier (Amersham Life Sciences). The reactions were conducted in 96-well plates at room temperature, in 0.1 ml of reaction buffer containing (final concentrations): 50 mM Tris-HCl, pH 7.5, 8.3 mM MgCl$_2$, 1.7 mM EGTA, [$^3$H]cAMP or [$^3$H]cGMP (approximately 2000 dpm/pmol), enzyme and various concentrations of the inhibitors. The assay was allowed to proceed for 1 hr and was terminated by adding 50 μl of SPA yttrium silicate beads in the presence of zinc sulfate. The plates were shaken and allowed to stand at room temperature for 20 min. Radiolabeled product formation was assessed by scintillation spectrometry.

[$^3$H]R-rolipram Binding Assay

The [$^3$H]R-rolipram binding assay was performed by modification of the method of Schneider and co-workers, see Nicholson, et al., Trends Pharmacol. Sci., Vol. 12, pp. 19–27 (1991) and McHale et al., Mol. Pharmacol., Vol. 39, 109–113 (1991). R-Rolipram binds to the catalytic site of PDE4 see Torphy et al., Mol. Pharmacol., Vol. 39, pp. 376–384 (1991). Consequently, competition for [$^3$H]R-rolipram binding provides an independent confirmation of the PDE4 inhibitor potencies of unlabeled competitors. The assay was performed at 30° C. for 1 hr in 0.5 μl buffer containing (final concentrations): 50 mM Tris-HCl, pH 7.5, 5 mM MgCl$_2$, 0.05% bovine serum lbumin, 2 nM [$^3$H]R-rolipram (5.7×104 dpm/pmol) and various concentrations of non-radiolabeled inhibitors. The reaction was stopped by the addition of 2.5 ml of ice-cold reaction buffer (without [$^3$H]-R-rolipram) and rapid vacuum filtration (Brandel Cell Harvester) through Whatman GF/B filters that had been soaked in 0.3% polyethylenimine. The filters were washed with an additional 7.5 ml of cold buffer, dried, and counted via liquid scintillation spectrometry.

The invention thus provides, in a further aspect, a combination comprising a compound of formula (I) or a physiologically acceptable salt or solvate thereof together with a PDE4 inhibitor.

The combination referred to above may conveniently be presented for use in the form of a pharmaceutical formulation and thus pharmaceutical formulations comprising a combination as defined above together with a pharmaceutically acceptable diluent or carrier represent a further aspect of the invention.

The compound according to the invention in combination with another therapeutically active ingredient as described above may be formulated for administration in any convenient way, and the invention therefore also includes within its scope pharmaceutical compositions comprising the compound of formula (I) or a physiologically acceptable solvate thereof in combination with another therapeutically active ingredient together, if desirable, in admixture with one or more physiologically acceptable diluents or carriers. The preferred route of administration for inflammatory disorders of the respiratory tract will generally be administration by inhalation.

The individual compounds of such combinations may be administered either sequentially in separate pharmaceutical compositions as well as simultaneously in combined pharmaceutical formulations. Appropriate doses of known therapeutic agents will be readily appreciated by those skilled in the art.

The compounds of formula (I) and salts and solvates thereof may be prepared by the methodology described hereinafter, constituting a further aspect of this invention.

A process according to the invention for preparing a compound of formula (I) or a salt or solvate thereof comprises alkylation of a thioacid of formula (II)

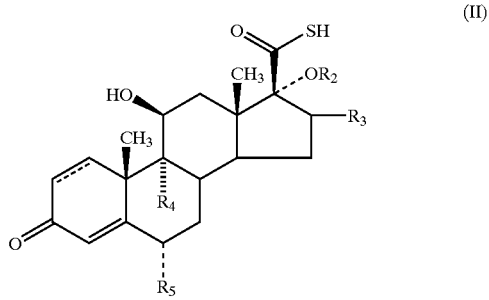

(II)

wherein R$^2$, R$^3$, R$^4$, R$^5$ and

----- are as defined above, or a salt thereof.

In this process the compound of formula (II) may be reacted with a compound of formula R$_1$-L wherein L represents a leaving group such as halogen atom or a tosyl or mesyl group or the like, for example, an appropriate alkyl orhaloalkyl halide under standard conditions.

Compounds of formula (II) may conveniently be employed as salts when such salts may be prepared in crystalline form.

When R₁ represents fluoromethyl, the preferred haloalkyl halide reagent is bromofluoromethane.

In a preferred process for preparing a compound of formula (I), a compound of formula (II) or a salt thereof may be treated with bromofluoromethane optionally in the presence of a phase transfer catalyst and optionally in the presence of an added base. A preferred solvent is methylacetate, or more preferably ethylacetate, optionally in the presence of water. The presence of water improves solubility of both starting material and product and the use of a phase transfer catalyst results in an increase in rate of reaction. Examples of phase transfer catalysts that may be employed include (but are not restricted to) tetrabutylammonium bromide, tetrabutylammonium chloride, benzyltributylammonium bromide, benzyltributylammonium chloride, benzyltriethylammonium bromide, methyltributylammonium chloride and methyltrioctylammonium chloride. THF may also advantageously be employed as solvent for the phase transfer catalyst.

Compounds of formula (II) may be prepared from the corresponding 17α-hydroxyl derivative of formula (III):

(III)

or a salt thereof wherein R³, R⁴, R₅ and

----- are as defined above, using for example, the methodology described by G. H. Phillipps et al., (1994) Journal of Medicinal Chemistry, 37, 3717–3729. For example the step typically comprises the addition of a reagent suitable for performing the esterification to the ester such as an aryl or heteroarylcarbonyl halide eg. 2-furanoyl chloride in the presence of a mild base eg. triethylamine. Generally the aryl or heteroarylcarbonyl halide would be employed in at least 2 times molar quantity relative to the compound of formula (III). The second mole of aryl or heteroarylcarbonyl halide tends to react with the thioacid moiety in the compound of formula (III) and would need to be removed by reaction with an amine such as diethylamine.

Compounds of formula (III) may be prepared in accordance with procedures described in GB 2088877B.

Compounds of formula (III) wherein R₃ represents methyl in the α configuration,

----- represents a double bond and R₄ and R₅ represent F may also be prepared by a process comprising the following steps:

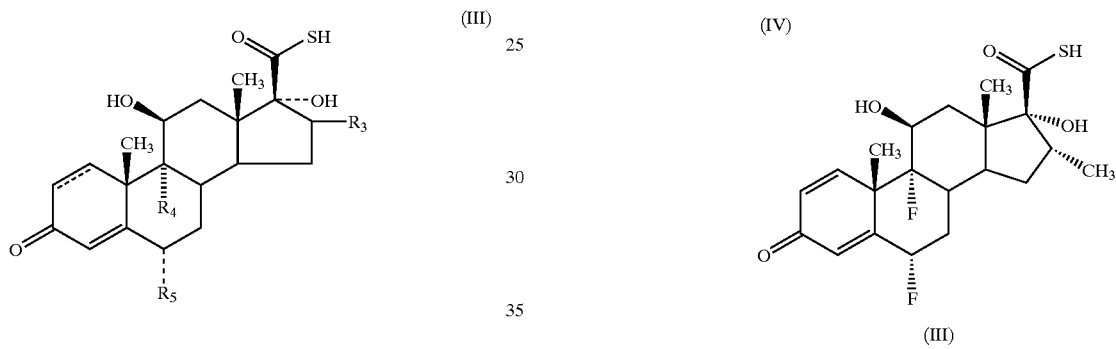

Step (a) comprises oxidation of a solution containing the compound of formula (V). Preferably, step (a) will be performed in the presence of a solvent comprising methanol, water, tetrahydrofuran, dioxan or diethylene glygol dimethylether. For example, so as to enhance yield and throughput, preferred solvents are methanol, water or tetrahydrofuran, and more preferably are water or tetrahydrofuran, especially water and tetrahydrofuran as solvent. Dioxan and diethylene glygol dimethylether are also preferred solvents which may optionally (and preferably) be employed together with water. Preferably, the solvent will be present in an amount of between 3 and 10 vol relative to the amount of the starting material (1 wt.), more preferably between 4 and 6 vol., especially 5 vol. Preferably the oxidising agent is present in an amount of 1–9 molar equivalents relative to the amount of the starting material. For example, when a 50% w/w aqueous solution of periodic acid is employed, the oxidising agent may be present in an amount of between 1.1 and 10 wt. relative to the amount of the starting material (1 wt.), more preferably between 1.1 and 3 wt., especially 1.3 wt. Preferably, the oxidation step will comprise the use of a chemical oxidising agent. More preferably, the oxidising agent will be periodic acid or iodic acid or a salt thereof. Most preferably, the oxidising agent will be periodic acid or sodium periodate, especially periodic acid. Alternatively (or in addition), it will also be appreciated that the oxidation step may comprise any suitable oxidation reaction, eg. one which utilises air and/or oxygen. When the oxidation reaction utilises air and/or oxygen, the solvent used in said reaction will preferably be methanol. Preferably, step (a)

will involve incubating the reagents at room temperature or a little warmer, say around 25° C. eg for 2 hours. The compound of formula (I) may be isolated by recrystallisation from the reaction mixture by addition of an anti-solvent. A suitable anti-solvent for compound of formula (I) is water. Surprisingly we have discovered that it is highly desirable to control the conditions under which the compound of formula (IV) is precipitated by addition of anti-solvent eg water. When the recrystallisation is performed using chilled water (eg water/ice mixture at a temperature of 0–5° C.) although better anti-solvent properties may be expected we have found that the crystalline product produced is very voluminous, resembles a soft gel and is very difficult to filter. Without being limited by theory we believe that this low density product contains a large amount of solvated solvent within the crystal lattice By contrast when conditions of around 10° C. or higher are used (eg around ambient temperature) a granular product of a sand like consistency which is very easily filtered is produced. Under these conditions, crystallisation typically commences after around 1 hour and is typically completed within a few hours (eg 2 hours). Without being limited by theory we believe that this granular product contains little or no of solvated solvent within the crystal lattice.

Step (b) will typically comprise the addition of a reagent suitable for converting a carboxylic acid to a carbothioic acid eg. using hydrogen sulphide gas together with a suitable coupling agent eg. carbonyldiimidazole (CDI) in the presence of a suitable solvent eg. dimethylformamide.

The aforementioned methodology may be adapted for the preparation of other compounds of formula (III).

An alternative process for preparing certain compounds of formula (II) comprises treating a compound of formula (X) with a reagent suitable for converting a carboxylic acid to a carbothioic acid eg using hydrogen sulphide gas together with a suitable coupling agent such as CDI in the presence of a suitable solvent eg DMF. Compounds of formula (X) may be prepared by methodology analogous to that described herein. Other compounds of formula (II) may be prepared similarly.

An alternative process for preparing a compound of formula (I) wherein $R_4$ represents fluorine or a salt or solvate thereof comprises reacting a compound of formula (VI)

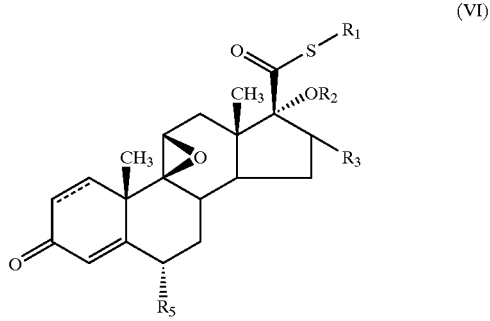

(VI)

with a fluorine source.

Examples of suitable sources of fluorine include fluoride (eg sodium fluoride) or, more preferably, HF. The preferred reagent is aqueous HF. A solvent such as THF or DMF may be employed.

A compound of formula (VI) may be prepared by a process comprising (a) alkylating a compound of formula (VII)

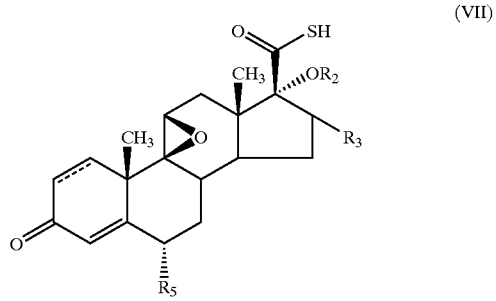

(VII)

or a salt thereof;

(b) reacting a compound of formula (VIII)

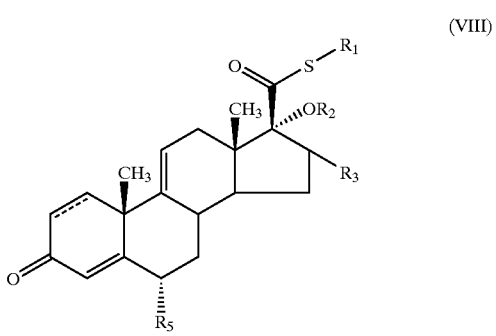

(VIII)

with an epoxide forming reagent; or (c) esterifying a compound of formula (IX)

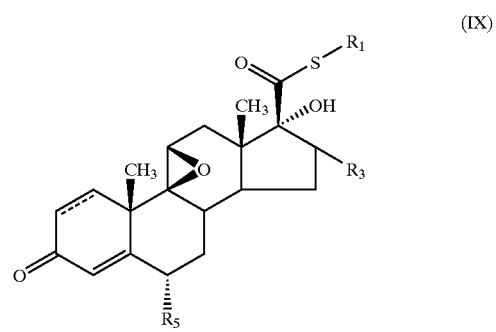

(IX)

In process (a), analogous conditions to those described above for the conversion of a compound of formula (II) to a compound of formula (I) may be employed. Typically compound of formula (VII) will be reacted with a compound of formula $R_1$-L wherein L represents a leaving group (eg a halogen atom, a mesyl or tosyl group or the like) for example, an appropriate fluoromethyl halide under standard conditions. Preferably, the fluoromethyl halide reagent is bromofluoromethane.

Process (b) is preferably performed in two steps: (i) formation of a halohydrin especially a bromohydrin (eg by reaction with bromodan or equivalent reagent), followed by (ii) treatment with base such as sodium hydroxide so as to effect ring closure. The product of step (i) is a compound of formula (IXA) which is a novel intermediate that may be isolated, if desired:

(IXA)

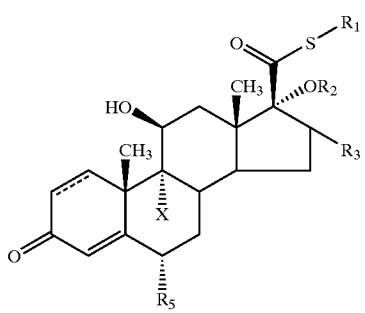

wherein X represents halogen, especially Br.

In process (c), a suitable reagent would be an activated derivative of an aryl or heteroaryl carboxylic acid such as an activated ester or preferably an acid halide eg an acid chloride in the presence of an organic base eg triethylamine. This reaction may be performed at elevated temperature eg around 60° C. or else at ambient temperature in the presence of an acylation catalyst eg dimethylamino pyridine (DMAP).

Compounds of formula (VII) may be prepared by a process comprising esterification of a compound of formula (XI)

(XI)

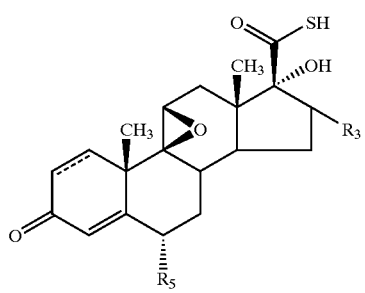

Analogous conditions to those described above for the conversion of a compound of formula (III) to a compound of formula (II) may be employed. For example, a suitable reagent would be an activated derivative of an aryl or heteroaryl carboxylic acid such as an activated ester or preferably an acid halide eg acid chloride in the presence of an organic base eg triethylamine. Certain compounds of formula (XI) are known (J Labelled Compd Radiopharm (1997) 39(7) 567–584) and others may be prepared by analogous methods.

A compound of formula (VIII) may be prepared by a process comprising (a) alkylating a compound of formula (XII)

(XII)

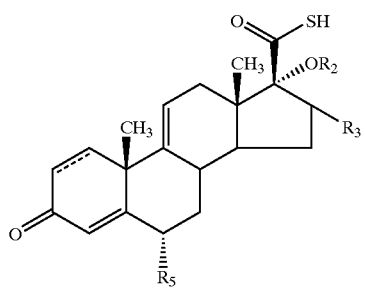

or a salt thereof; or (b) esterifying a compound of formula (XIII)

(XIII)

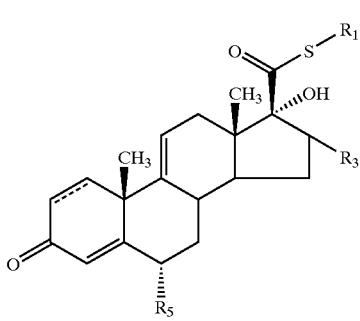

In process (a), analogous conditions to those described above for the conversion of a compound of formula (II) to a compound of formula (I) may be employed. Typically compound of formula (XII) will be reacted with a compound of formula $R_1$-L wherein L represents a leaving group (eg a halogen atom, a mesyl or tosyl group or the like) for example, an appropriate fluoromethyl halide under standard conditions. Preferably, the fluoromethyl halide reagent is bromofluoromethane.

In process (b), analogous conditions to those employed above for the conversion of a compound of formula (IX) to a compound of formula (VI) may be employed. For example, a suitable reagent would be an activated derivative of an aryl or heteroaryl carboxylic acid such as an activated ester or preferably an acid halide eg acid chloride in the presence of an organic base eg triethylamine.

Compounds of formula (IX) and (XIII) may be prepared by alkylating the corresponding thioacids (XI) and (XIV) (defined below) using methodology analogous to that already described (eg by reaction with a compound of formula $FCH_2L$ wherein L represents a leaving group (eg a halogen atom, a mesyl or tosyl group or the like) for example, an appropriate fluoromethyl halide under standard conditions. Preferably, the fluoromethyl halide reagent is bromofluoromethane. Thethioacids (XI) are either known compounds (J Labelled Compd Radiopharm (1997) 39(7) 567–584) or may be prepared by analogous methods.

Compounds of formula (XII) may be prepared by a process comprising esterifying a compound of formula (XIV):

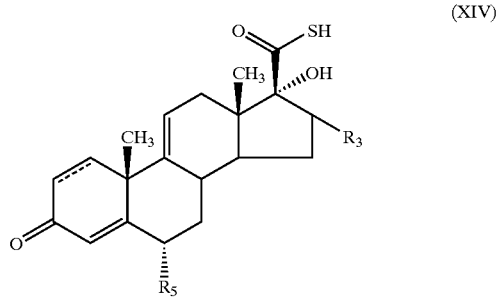
(XIV)

or a salt thereof.

This process may be performed using methodology analogous to that already described. For example, a suitable reagent would be an activated derivative of an aryl or heteroaryl carboxylic acid such as an activated ester or preferably an acid halide eg and acid chloride in the presence of an organic base eg triethylamine.

Compounds of formula (XIV) may be prepared from the corresponding carboxylic acid eg by a process analogous to that described above for the conversion of a compound of formula (IV) to a compound of formula (III). The aforesaid the corresponding carboxylic acid is either known (Upjohn WO90/15816) or may be prepared by conventional methods.

A further alternative process for preparing a compound of formula (I) or a salt or solvate thereof comprises deprotecting or unmasking a compound of formula (I) in which the 11-β-hydroxy group is protected or masked. A first such process comprises deprotecting a compound of formula (XV)

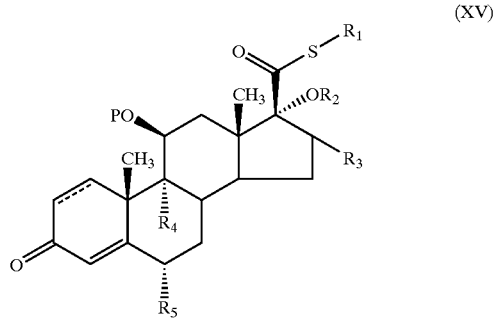
(XV)

wherein P represents a hydroxy protecting group.

Examples of hydroxy protecting groups P are described in Protective Groups in Organic Chemistry Ed J F W McOmie (Plenum Press 1973) or Protective Groups in Organic Synthesis by Theodora W Green (John Wiley and Sons, 1991).

Examples of suitable hydroxy protecting groups P include groups selected from carbonate, alkyl (eg t-butyl or methoxymethyl), aralkyl (eg benzyl, p-nitrobenzyl, diphenylmethyl or triphenylmethyl), heterocyclic groups such as tetrahydropyranyl, acyl (eg acetyl or benzyl) and silyl groups such as trialkylsilyl (eg t-butyldimethylsilyl). The hydroxy protecting groups may be removed by conventional techniques. Thus, for example, carbonate may be removed by treatment with base and alkyl, silyl, acyl and heterocyclic groups may be removed by solvolysis eg by hydrolysis under acid or basic conditions. Aralkyl groups such as triphenylmethyl may similarly be removed by solvolysis eg by hydrolysis under acidic conditions. Aralkyl groups such as benzyl or p-nitrobenzyl may be cleaved by hydrogenolysis in the presence of a Noble metal catalyst such as palladium on charcoal. p-Nitrobenzyl may also be cleaved by photolysis.

The 11-β-hydroxy group may be masked as a carbonyl group. Thus a second such process comprises reduction of a compound of formula (XVI)

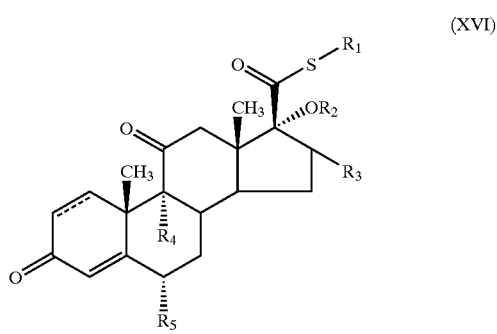
(XVI)

Reduction to the compound of formula (I) may be achieved eg by treatment with a hydride reducing agent such as borohydride eg sodium borohydride The 11-ketone (XVI) may also be masked. Examples of masked derivatives of compound of formula (XVI) include (i) ketal derivatives eg ketals formed by treatment of the compound of formula (XVI) with an alcohol eg methanol, ethanol or ethan-1,2-diol, (ii) dithioketal derivatives eg dithioketals formed by treatment of a compound of formula (XVI) with a thiol eg methanethiol, ethanethiol or ethan-1, 2-dithiol, (iii) monothioketal derivatives eg monothioketals formed by treatment of a compound of formula (XVI) with eg 1-hydroxy-ethane-2-thiol, (iv) derivatives formed by treatment of a compound of formula (XVI) with an alcoholamine eg ephedrine, (v) imines formed by treatment of a compound of formula (XVI) with amines, (vi)oximes formed by treatment of compounds of formula (XVI) with hydroxylamines. We claims such derivatives of compounds of formula (XVI) as an aspect of the invention.

These masked derivatives may be converted back to the ketone by conventional means eg ketals, imines and oximes are converted to carbonyl by treatment with dilute acid and dithioketals are converted to the ketone by a variety of methods as described by P. C. Bulman Page et al (1989), Tetrahedron, 45, 7643–7677 and references therein.

Compounds of formula (XV) may be prepared by a process comprising (a) alkylating a compound of formula (XVII)

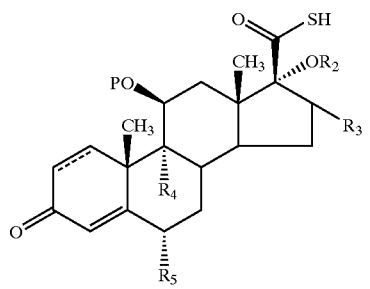
(XVII)

or a salt thereof wherein P represents a hydroxy protecting group; or (b) esterifying a compound of formula (XVIII)

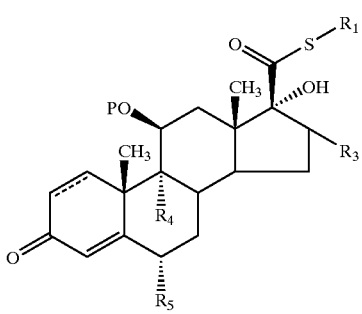
(XVIII)

In step (a), analogous conditions to those described above for the conversion of a compound of formula (II) to a compound of formula (I) may be employed. Typically compound of formula (XVII) will be reacted with a compound of formula $R_1$-L wherein L represents a leaving group (eg a halogen atom, a mesyl or tosyl group or the like) for example, an appropriate fluoromethyl halide under standard conditions. Preferably, the fluoromethyl halide reagent is bromofluoromethane.

In step (b), analogous conditions to those employed above for the conversion of a compound of formula (IX) to a compound of formula (VI) may be employed. For example, a suitable reagent would be an activated derivative of an aryl or heteroaryl carboxylic acid such as an activated ester or preferably an acid halide eg acid chloride in the presence of an organic base eg triethylamine.

Compound of formula (XVIII) may be prepared by alkylating the corresponding thioacid using methodology analogous to that already described (eg by reaction with a compound of formula $R_1$-L wherein L represents a leaving group (eg a halogen atom, a mesyl or tosyl group or the like) for example, an appropriate fluoromethyl halide under standard conditions. When $R_1$ represents —$CH_2F$, preferably, the fluoromethyl halide reagent is bromofluoromethane. The corresponding thioacids are known compounds or may be prepared by known methods. Compound of formula (XVIII) may alternatively be prepared by protection of the corresponding hydroxy derivative.

Compound of formula (XVII) may be prepared by a process comprising esterifying a compound of formula (XIX)

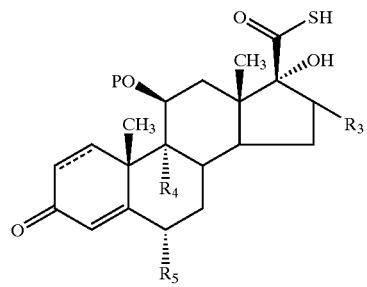
(XIX)

or a salt thereof wherein P represents a hydroxy protecting group.

This process may be performed using methodology analogous to that already described. For example, a suitable reagent would be an activated derivative of an aryl or heteroaryl carboxylic acid such as an activated ester or preferably an acid halide eg acid chloride in the presence of an organic base eg triethylamine.

Compounds of formula (XIX) may be prepared by protecting the corresponding hydroxy derivative, having first protected the thioacid which would need to be subsequently deprotected. The corresponding hydroxy derivatives are known compounds or may be prepared by known methods.

Compounds of formula (XVI) may be prepared by a process comprising (a) alkylating a compound of formula (XX)

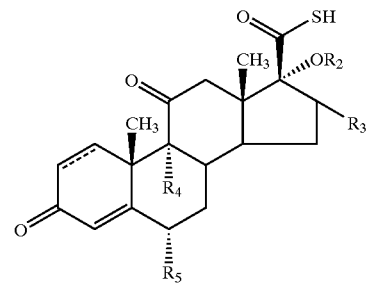
(XX)

or a salt thereof or a derivative wherein the 11-carbonyl group is masked; or (b) esterifying a compound of formula (XXI)

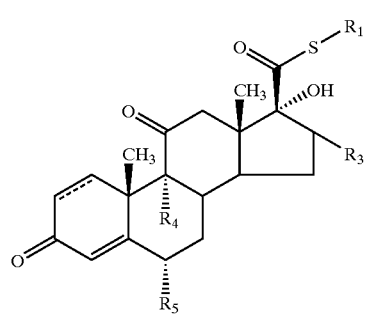
(XXI)

or a derivative wherein the 11-carbonyl group is masked.

In step (a), analogous conditions to those described above for the conversion of a compound of formula (III) to a compound of formula (II) may be employed. Typically compound of formula (XX) will be reacted with a compound of formula R$_1$-L wherein L represents a leaving group (eg a halogen atom, a mesyl or tosyl group or the like) for example, an appropriate fluoromethyl halide under standard conditions. Preferably, the fluoromethyl halide reagent is bromofluoromethane.

In step (b), analogous conditions to those employed above for the conversion of a compound of formula (IX) to a compound of formula (VI) may be employed. For example, a suitable reagent would be an activated derivative of an aryl or heteroaryl carboxylic acid such as an activated ester or preferably an acid halide eg acid chloride in the presence of an organic base eg triethylamine.

Compound of formula (XXI) or a derivative thereof wherein the 11-ketone group is masked may be prepared by alkylating the corresponding thioacid using methodology analogous to that already described (eg by reaction with a compound of formula R$_1$-L wherein L represents a leaving group (eg a halogen atom, a mesyl or tosyl group or the like) for example, an appropriate fluoromethyl halide under standard conditions. Preferably, the fluoromethyl halide reagent is bromofluoromethane. The corresponding thioacids are known compounds.

Compound of formula (XX) may be prepared by a process comprising esterifying a compound of formula (XXII)

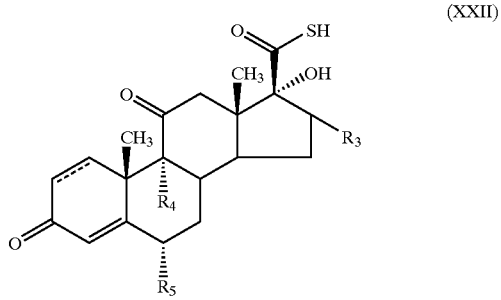

(XXII)

or a salt thereof or a derivative thereof wherein the 11-ketone group is masked.

This process may be performed using methodology analogous to that already described. For example, a suitable reagent would be an activated derivative of an aryl or heteroaryl carboxylic acid such as an activated ester or preferably an acid halide eg acid chloride in the presence of an organic base eg triethylamine.

Compounds of formula (XXII) and derivatives thereof wherein the 11-ketone is masked may be prepared by oxidation of the corresponding hydroxy derivative (IV) (or analogue thereof) followed by masking of the ketone and subsequent conversion of the carboxylic acid group to the thioacid (see eg conversion of compounds of formula (IV) to (III)).

A further alternative process for the preparation of compounds of formula (I) wherein R$_1$ represents —CH$_2$F comprises reaction of a compound of formula (XXIII)

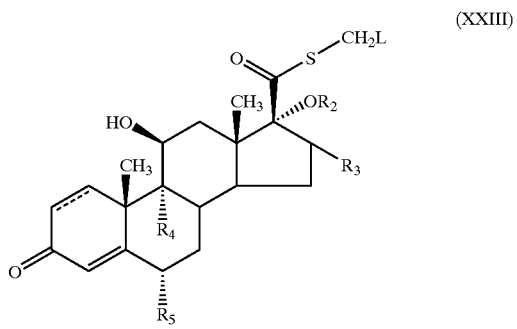

(XXIII)

wherein L represents a leaving group (eg halide other than fluoride such as chloride, iodide or a sulphonate ester such mesylate, tosylate, triflate) with a fluorine source.

Preferably the fluorine source is fluoride ion eg KF. Further details for this conversion may be obtained by reference to G. H. Phillipps et al., (1994) Journal of Medicinal Chemistry, 37, 3717–3729 or J Labelled Compd Radiopharm (1997) 39(7) 567–584).

Some compounds of formula (XXIII) are compounds of formula (I). Compounds of formula (XXIII) may be prepared by methods analogous to those described herein. Corresponding novel intermediates of formula (VI), (VII), (IX), (IXA), (XV) and (XVI) wherein the —CH$_2$F moiety is replaced with a —CH$_2$L moiety (wherein L represents a leaving group other than fluorine) are claimed as an aspect of the invention.

A further alternative process for the preparation of compounds of formula (I) or a solvate thereof comprises deprotection or unmasking of a derivative of a compound of formula (I) in which the 3-carbonyl group is protected or masked.

The 3-carbonyl group may be masked in a manner analogous to that described above in relation to masking of the 11-carbonyl position. Thus the 3-carbonyl may be masked eg as a ketal, monothioketal, dithioketal, derivative with an alcoholamine, oxime or imine. The carbonyl group may be recovered by conventional means eg ketals are converted to carbonyl by treatment with dilute acid and dithioketals are converted to the ketone by a variety of methods as described by P. C. Bulman Page et al (1989), Tetrahedron, 45, 7643–7677 and references therein.

Certain intermediate compounds are new and we provide these, together where appropriate with their salts and solvates, as an aspect of the invention.

The advantages of the compounds of formula (I) and/or its solvates may include the fact that the substance appears to demonstrate excellent anti-inflammatory properties, with predictable pharmacokinetic and pharmacodynamic behaviour, with an attractive side-effect profile, long duration of action, and is compatible with a convenient regime of treatment in human patients, in particular being amendable to once-per day dosing. The advantages may be appreciated in particular when the compound of formula (I) and/or its solvates are employed in combinatoin with a the long-acting β$_2$-adrenoreceptor agonist. Further advantages may include the fact that the substance has desirable physical and chemical properties which allow for ready manufacture and storage.

The following non-limiting Examples illustrate the invention:

EXAMPLES

General $^1$H-nmr spectra were recorded at 400 MHz and the chemical shifts are expressed in ppm relative to tetramethylsilane. The following abbreviations are used to describe the multiplicities of the signals: s (singlet), d (doublet), t (triplet), q (quartet), m (multiplet), dd (doublet of doublets), dt (doublet of triplets) and b (broad). Biotage refers to prepacked silica gel cartridges containing KP-Sil run on flash 12i chromatography module. LCMS was conducted on a Supelcosil LCABZ+PLUS column (3.3 cm×4.6 mm ID) eluting with 0.1% $HCO_2H$ and 0.01 M ammonium acetate in water (solvent A), and 0.05% $HCO_2H$ 5% water in acetonitrile (solvent B), using the following elution gradient 0–0.7 min 0% B, 0.7–4.2 min 100% B, 4.2–5.3 min 0% B, 5.3–5.5 min 0% B at a flow rate of 3 ml/min. The mass spectra were recorded on a Fisons VG Platform spectrometer using electrospray positive and negative mode (ES+ve and ES−ve).

Intermediates

Intermediate 1: 6α,9α-Difluoro-17α[(2-furanylcarbonyl)oxy]-11β-hydroxy-16α-methyl-3-oxo-androsta-1,4-diene-17β-carbothioic Acid A solution of 6α, 9α-difluoro-11β, 17α-dihydroxy-16α-methyl-3-oxo-androsta-1,4-diene-17β-carbothioic acid (prepared in accordance with the procedure described in GB 2088877B) (18 g, 43.64 mmol) in anhydrous dichloromethane (200 ml) and triethylamine (15.94 ml, 114 mmol) was treated at <5° C. with a solution of 2-furoyl chloride (11.24 ml, 114 mmol) in anhydrous dichloromethane (100 ml) over approximately 40 min. The solution was stirred at <5° C. for 30 min. The resulting solid was collected by filtration, washed successively with 3.5% aqueous sodium hydrogen carbonate solution, water, 1M hydrochloric acid, and water and dried in vacuo at 60° C. to give a cream coloured solid. The dichloromethane filtrate was washed successively with 3.5% sodium hydrogen carbonate solution, water, 1M hydrochloric acid, water, dried ($Na_2SO_4$) and evaporated to give a cream coloured solid which was combined with that isolated above. The combined solids (26.9 g) were suspended in acetone (450 ml) and stirred. Diethylamine (16.8 ml, 162 mmol) was added and the mixture stirred at room temperature for 4.5 h. The mixture was concentrated and the precipitate collected by filtration and washed with a little acetone. The washings and filtrate were combined, concentrated and loaded onto a silica gel Biotage column which was eluted with 24:1 chloroform:methanol. Fractions which contained the more polar component were combined and evaporated to give a cream coloured solid. This was combined with the solid isolated above and dried in vacuo to give a pale beige coloured solid (19.7 g). This was dissolved in warm water, the pH adjusted to 2 with concentrated hydrochloric acid and the mixture extracted with ethyl acetate. The organic extract was dried ($Na_2SO_4$) and evaporated to give, after drying at 50° C., the title compound as a cream coloured solid (18.081 g, 82%): LCMS retention time 3.88 min, m/z 507 MH$^+$, NMR δ ($CDCl_3$) includes 7.61 (1H, m), 7.18–7.12 (2H, m), 6.52 (1H, dd, J 4, 2 Hz), 6.46 (1H, s), 6.41 (1H, dd, J 10, 2 Hz), 5.47 and 5.35 (1H, 2 m), 4.47 (1H, bd, J 9 Hz), 3.37 (1H, m), 1.55 (3H, s), 1.21 (3H, s), 1.06 (3H, d, J 7 Hz).

The following intermediates were prepared using a method analogous to that described for Intermediate 1:

Intermediate 2: 6α,9α-Difluoro-17α[(3-furanylcarbonyl)oxy]-11β-hydroxy-16α-methyl-3-oxo-androsta-1,4-diene-17β-carbothioic acid LCMS retention time 3.75 min, m/z 507 MH$^+$.

Intermediate 3: 6α,9α-Difluoro-11β-hydroxy-16α-methyl-3-oxo-17α-[(2-thienylcarbonyl)oxy]-androsta-1,4-diene-17β-carbothioic acid LCMS retention time 3.93 min, m/z 523 MH$^+$.

Intermediate 4: 6α,9α-Difluoro-11β-hydroxy-16α-methyl-3-oxo-17α-[(3-thienylcarbonyl)oxy]-androsta-1,4-diene-17β-carbothioic acid LCMS retention time 3.95 min, m/z 523 MH$^+$.

Intermediate 5: 17α-(Benzoyl)oxy-6α,9α-difluoro-11β-hydroxy-16α-methyl-3-oxo-androsta-1,4-diene-17β-carbothioic acid LCMS retention time 4.02 min, m/z 517 MH$^+$.

Intermediate 6: 9α-Fluoro-17α-[(2-furanylcarbonyl)oxy]-11β-hydroxy-16β-methyl-3-oxo-androsta-1,4-diene-17β-carbothioic acid Intermediate 6 was prepared from 11β,17α-dihydroxy-9α-fluoro-16β-methyl-3-oxo-androsta-1,4-diene-17β-carbothioic acid (prepared in accordance with the procedure described in Phillips et al, (1994) J. Med. Chem. 37, 3717–3729). LCMS retention time 3.61 min, m/z 489 MH$^+$.

Intermediate 7: 6α,9α-Difluoro-11β-hydroxy-16α-methyl-17α-[(5-methylthiophene-2-carbonyl)oxy]-3-oxo-androsta-1,4-diene-17β-carbothioic acid LCMS retention time 4.01 min, m/z 537 MH$^+$ Intermediate 8: 6α,9α-Difluoro-11β-hydroxy-17α-[(isoxazole-5-carbonyl)oxy]-16α-methyl-3-oxo-androsta-1,4-diene-17β-carbothioic acid LCMS retention time 3.69 min, m/z 508 MH$^+$ Intermediate 9: 17α-[(5-Chlorothiophene-2-carbonyl)oxy]-6α,9α-difluoro-11β-hydroxy-16α-methyl-3-oxo-androsta-1,4-diene-17β-carbothioic acid LCMS retention time 4.36 min, m/z 557/559 MH$^+$ Intermediate 10: 6α,9α-Difluoro-17α-[(3,5-dimethylisoxazole-4-carbonyl)oxy]-11β-hydroxy-16α-methyl-3-oxo-androsta-1,4-diene-17β-carbothioic acid LCMS retention time 3.71 min, m/z 536 MH$^+$ Intermediate 11: 17α-[(5-Chloro-4-methoxy-thiophene-3-carbonyl)oxy]-6α,9α-difluoro-11β-hydroxy-16α-methyl-3-oxo-androsta-1,4-diene-17β-carbothioic acid LCMS retention time 4.18 min, m/z 587/589 MH$^+$ Intermediate 12: 6α,9α-Difluoro-11β-hydroxy-16α-methyl-17α-[(4-methyl-1,2,3-thiadiazole-5-carbonyl)oxy]-3-oxo-androsta-1,4-diene-17β-carbothioic acid LCMS retention time 4.06 min, m/z 539 MH$^+$ Intermediate 13: 17α-[(3-Bromothiophene-2-carbonyl)oxy]-6α,9α-difluoro-11β-hydroxy-16α-methyl-3-oxo-androsta-1,4-diene-17β-carbothioic acid LCMS retention time 4.31 min, m/z 601/603 MH$^+$ Intermediate 14: 17α-[(2,5-Dichlorothiophene-3-carbonyl)oxy]-6α,9α-difluoro-11β-hydroxy-16α-methyl-3-oxo-androsta-1,4-diene-17β-carbothioic acid LCMS retention time 4.59 min, m/z 591/593/595 MH$^+$ Intermediate 15: 17α-[(5-Bromofuran-2-carbonyl)oxy]-6α,9α-difluoro-11β-hydroxy-16α-methyl-3-oxo-androsta-1,4-diene-17β-carbothioic acid LCMS retention time 4.14 min, m/z 585/587 MH$^+$ Intermediate 16: 6α,9α-Difluoro-17α-[(2,5-dimethylfuran-3-carbonyl)oxy]-11β-hydroxy-16α-methyl-3-oxo-androsta-1,4-diene-17β-carbothioic acid LCMS retention time 4.02 min, m/z 535 MH$^+$ Intermediate 17: 17α-[(3-Chlorothiophene-2-carbonyl)oxy]-6α,9α-difluoro-11β-hydroxy-16α-methyl-3-oxo-androsta-1,4-diene-17β-carbothioic acid LCMS retention time 4.27 min, m/z 557/559 MH$^+$ Intermediate 18: 6α,9α-Difluoro-11β-hydroxy-16α-methyl-17α-[(2-methylfuran-3-carbonyl)oxy]-3-oxo-androsta-1,4-diene-17β-carbothioic acid LCMS retention time 3.92 min, m/z 521 MH⁺

Intermediate 19: 6α,9α-Difluoro-11β-hydroxy-16α-methyl-17α-[(3-methylfuran-2-carbonyl)oxy]-3-oxo-androsta-1,4-diene-17β-carbothioic acid LCMS retention time 3.85 min, m/z 521 MH⁺

Intermediate 20: 6α,9α-Difluoro-11β-hydroxy-16α-methyl-17α-[(5-methylisoxazole-4-carbonyl)oxy]-3-oxo-androsta-1,4-diene-17β-carbothioic acid LCMS retention time 3.74 min, m/z 522 MH⁺

Intermediate 21: 6α,9α-Difluoro-11β-hydroxy-16α-methyl-17α-[(1-methyl-1H-pyrrole -2-carbonyl)oxy]-3-oxo-androsta-1,4-diene-17β-carbothioic acid LCMS retention time 3.78 min, m/z 520 MH⁺

Intermediate 22: 6α,9α-Difluoro-11β-hydroxy-16α-methyl-3-oxo-17α-[(1,3-thiazole-4-carbonyl)oxy]-androsta-1,4-diene-17β-carbothioic acid LCMS retention time 3.48 min, m/z 524 MH⁺

Intermediate 23: 6α,9α-Difluoro-17α-[(2,4-dimethyl-1,3-thiazole-5-carbonyl)oxy]-11β-hydroxy-16α-methyl-3-oxo-androsta-1,4-diene-17β-carbothioic acid LCMS retention time 3.72 min, m/z 552 MH⁺

Intermediate 24: 6α,9α-Difluoro-11β-hydroxy-16α-methyl-17α-[(5-methylisoxazole-3-carbonyl)oxy]-3-oxo-androsta-1,4-diene-17β-carbothioic acid LCMS retention time 3.72 min, m/z 522 MH⁺

Intermediate 25: 6α,9α-Difluoro-11β-hydroxy-16α-methyl-17α-[(3-methylisoxazole-5-carbonyl)oxy]-3-oxo-androsta-1,4-diene-17β-carbothioic acid LCMS retention time 3.84 min, m/z 522 MH⁺

Intermediate 26: 6α,9α-Difluoro-17α-[(1,3-dimethyl-1H-pyrazole-5-carbonyl)oxy]-11β-hydroxy-16α-methyl-3-oxo-androsta-1,4-diene-17β-carbothioic acid LCMS retention time 3.72 min, m/z 535 MH⁺

Intermediate 27: 6α,9α-Difluoro-11β-hydroxy-16α-methyl-3-oxo-17α-[(1,2,3-thiadiazole-5-carbonyl)oxy]-androsta-1,4-diene-17β-carbothioic acid LCMS retention time 3.89 min, m/z 525 MH⁺

Intermediate 28: 6α,9α-Difluoro-11β-hydroxy-17α-[(isoxazole-3-carbonyl)oxy]-16α-methyl-3-oxo-androsta-1,4-diene-17β-carbothioic acid LCMS retention time 3.78 min, m/z 508 MH⁺

Intermediate 29: 6α,9α-Difluoro-11β-hydroxy-17α-[(4-methoxy-thiophene-3-carbonyl)oxy]-16α-methyl-3-oxo-androsta-1,4-diene-17β-carbothioic acid LCMS retention time 3.74 min, m/z 553 MH⁺

Intermediate 30 6α,9α-Difluoro-11β-hydroxy-16α-methyl-17α-[(2-methyl-1,3-thiazole-4-carbonyl)oxy]-3-oxo-androsta-1,4-diene-17β-carbothioic acid LCMS retention time 3.70 min, m/z 538 MH⁺

Intermediate 31: 6α,9α-Difluoro-17α-[(3-ethoxy-thiophene-2-carbonyl)oxy]-11β-hydroxy-16α-methyl-3-oxo-androsta-1,4-diene-17β-carbothioic acid LCMS retention time 3.85 min, m/z 567 MH⁺

Intermediate 32: 6α,9α-Difluoro-11β-hydroxy-16α-methyl-3-oxo-17α-[(1,2,3-thiadiazole-4-carbonyl)oxy]-androsta-1,4-diene-17β-carbothioic acid LCMS retention time 3.70 min, m/z 526 MH⁺

Intermediate 33: 6α,9α-Difluoro-11β-hydroxy-16α-methyl-3-oxo-17α-[(1H-pyrrole-2-carbonyl)oxy]-androsta-1,4-diene-17β-carbothioic acid LCMS retention time 3.75 min, m/z 506 MH⁺

Intermediate 34: 6α,9α-Difluoro-11β-hydroxy-16α-methyl-3-oxo-17α-[(1,3-thiazole-5-carbonyl)oxy]-androsta-1,4-diene-17β-carbothioic acid LCMS retention time 4.29 min, m/z 524 MH⁺

Intermediate 35: 6α,9α-Difluoro-11β-hydroxy-16α-methyl-3-oxo-17α-[(1,2,5-thiadiazole-3-carbonyl)oxy]-androsta-1,4-diene-17β-carbothioic acid LCMS retention time 4.65 min, m/z 525 MH⁺

Intermediate 36: 6α,9α-Difluoro-11β-hydroxy-17α-[(isothiazole-3-carbonyl)oxy]-16α-methyl-3-oxo-androsta-1,4-diene-17β-carbothioic acid LCMS retention time 4.44 min, m/z 524 MH⁺

Intermediate 37: 6α,9α-Difluoro-11β-hydroxy-17α-[(isothiazole-5-carbonyl)oxy]-16α-methyl-3-oxo-androsta-1,4-diene-17β-carbothioic acid LCMS retention time 4.60 min, m/z 524 MH⁺

Intermediate 38: 6α,9α-Difluoro-11β-hydroxy-16α-methyl-17α-[(3-methylthiophene-2-carbonyl)oxy]-3-oxo-androsta-1,4-diene-17β-carbothioic acid LCMS retention time 4.31 min, m/z 537 MH⁺

Intermediate 39: 6α,9α-Difluoro-11β-hydroxy-16α-methyl-17α-[(4-methyl-1,3-thiazole-5-carbonyl)oxy]-3-oxo-androsta-1,4-diene-17β-carbothioic acid LCMS retention time 4.19 min, m/z 538 MH⁺

Intermediate 40: 17α-[(1-Ethyl-3-methyl-1H-pyrazole-5-carbonyl)oxy]-6α,9α-difluoro-11β-hydroxy-16α-methyl-3-oxo-androsta-1,4-diene-17β-carbothioic acid LCMS retention time 4.33 min, m/z 549 MH⁺

Intermediate 41: 6α,9α-Difluoro-17α-[(1-methyl-1H-imidazole-5-carbonyl)oxy]-11β-hydroxy-16α-methyl-3-oxo-androsta-1,4-diene-17β-carbothioic acid LCMS retention time 3.91 min, m/z 521 MH⁺

EXAMPLES

Example 1

6α,9α-Difluoro-17α-[(2-furanylcarbonyl)oxy]-11β-hydroxy-16α-methyl-3-oxo-androsta-1,4-diene-17β-carbothioic acid S-fluoromethyl ester A suspension of Intermediate 1 (2.5 g, 4.94 mmol) was dissolved in anhydrous N,N-dimethylformamide (25 ml) and sodium hydrogen carbonate (465 mg, 5.53 mmol) was added. The mixture was stirred at −20° C. and bromofluoromethane (0.77 ml, 6.37 mmol) was added and the mixture was stirred at −20° C. for 2 h. Diethylamine (2.57 ml, 24.7 mmole) was added and the mixture stirred at −20° C. for 30 min. The mixture was added to 2M hydrochloric acid (93 ml) and stirred for 30 min. Water (300 ml) was added and the precipitate was collected by filtration, washed with water and dried in vacuo at 50° C. to give a white solid which was recrystallised from acetone/water and dried in vacuo at 50° C. to give the title compound(2.351 g, 88%): LCMS retention time 3.66 min, m/z 539 MH⁺, NMR δ (CDCl₃) includes 7.60 (1H, m), 7.18–7.11 (2H, m), 6.52 (1H, dd, J 4.2 Hz), 6.46 (1H, s), 6.41 (1H, dd, J 10, 2 Hz), 5.95 and 5.82 (2H dd, J 51, 9 Hz), 5.48 and 5.35 (1H, 2 m), 4.48 (1H, m), 3.48 (1H, m), 1.55 (3H, s), 1.16 (3H, s), 1.06 (3H, d, J 7 Hz).

Example 2

6α,9α-Difluoro-17α-[(3-furanylcarbonyl)oxy]-11β-hydroxy-16α-methyl-3-oxo-androsta-1,4-diene-17β-carbothioic acid S-fluoromethyl ester Example 2 was prepared from Intermediate 2 using a method analogous to that described for Example 1.

LCMS retention time 3.72 min, m/z 539 MH⁺.

Example 3

6α,9α-Difluoro-11β-hydroxy-16α-methyl-3-oxo-17α-[(2-thienylcarbonyl)oxy]-androsta-1,4-diene-17β-carbothioic acid S-fluoromethyl ester Example 3 was prepared from Intermediate 3 using a method analogous to that described for Example 1.

LCMS retention time 3.81 min, m/z 555 MH⁺.

Example 4

6α,9α-Difluoro-11β-hydroxy-16α-methyl-3-oxo-17α-[(3-thienylcarbonyl)oxy]-androsta-1,4-diene-17β-carbothioic acid S-fluoromethyl ester Example 4 was prepared from Intermediate 4 using a method analogous to that described for Example 1.
LCMS retention time 3.82 min, m/z 555 MH$^+$.

Example 5

17α-(Benzoyl)oxy-6α,9α-Difluoro-11β-hydroxy-16α-methyl-3-oxo-androsta-1,4-diene-17-carbothioic acid S-fluoromethyl ester Example 5 was prepared from Intermediate 5 using a method analogous to that described for Example 1.
LCMS retention time 3.73 min, m/z 549 MH$^+$.

Example 6

9α-Fluoro-17α-[(2-furanylcarbonyl)oxy]-11β-hydroxy-16β-methyl-3-oxo-androsta-1,4-diene-17β-carbothioic acid S-fluoromethyl ester Example 6 was prepared from Intermediate 6 using a method analogous to that described for Example 1.
LCMS retention time 3.61 min, m/z 521 MH$^+$.

Example 7

6α,9α-Difluoro-17α-[(2-furanylcarbonyl)oxy]-11β-hydroxy-16α-methyl-3-oxo-androst-4-ene-17β-carbothioic acid S-fluoromethyl ester A solution of Example 1 (500 mg, 0.93 mmol) and Wilkinson's catalyst (150 mg) in a mixture of toluene (14 ml) and ethanol (7 ml) was stirred in an atmosphere of hydrogen for 23 h. The solution was evaporated to dryness and the residue purified by Biotage chromatography using ethyl acetate:petroleum ether (1:2) as eluant to give a yellow solid (435 mg) which was recrystallised (ethyl acetate/petroleum ether) to give the title compound (364 mg, 72%).
LCMS retention time 3.57 min, m/z 541 MH$^+$.

Example 8

6α,9α-Difluoro-11α-hydroxy-17α-[(isoxazole-5-carbonyl)oxy]-16α-methyl-3-oxo-androsta-1,4-diene-17β-carbothioic acid S-fluoromethyl ester Example 8 was prepared from Intermediate 8 using a method analogous to that described for Example 1: LCMS retention time 3.47 min, m/z 540 MH$^+$

Example 9

17α-[(5-Chlorothiophene-2-carbonyl)oxy]-6α,9α-difluoro-11β-hydroxy-16α-methyl-3-oxo-androsta-1,4-diene-17β-carbothioic acid S-fluoromethyl ester Example 9 was prepared from Intermediate 9 using a method analogous to that described for Example 1: LCMS retention time 3.89 min, m/z 589/591 MH$^+$

Example 10

6α,9α-Difluoro-17α-[(3,5-dimethylisoxazole-4-carbonyl)oxy]-11β-hydroxy-16α-methyl-3-oxo-androsta-1,4-diene-17β-carbothioic acid S-fluoromethyl ester Example 10 was prepared from Intermediate 10 using a method analogous to that described for Example 1: LCMS retention time 3.70 min, m/z 568 MH$^+$

Example 11

17α-[(5-Chloro-4-methoxy-thiophene-3-carbonyl)oxy]-6α,9α-difluoro-11β-hydroxy-16α-methyl-3-oxo-androsta-1,4-diene-17β-carbothioic acid S-fluoromethyl ester Example 11 was prepared from Intermediate 11 using a method analogous to that described for Example 1: LCMS retention time 3.99 min, m/z 619/621 MH$^+$

Example 12

6α,9α-Difluoro-11β-hydroxy-16α-methyl-17α-[(4-methyl-1,2,3-thiadiazole-5-carbonyl)oxy]-3-oxo-androsta-1,4-diene-17β-carbothioic acid S-fluoromethyl ester Example 12 was prepared from Intermediate 12 using a method analogous to that described for Example 1: LCMS retention time 3.74 min, m/z 571 MH$^+$

Example 13

17α-[(3-Bromothiophene-2-carbonyl)oxy]-6α,9α-difluoro-11β-hydroxy-16α-methyl-3-oxo-androsta-1,4-diene-17β-carbothioic acid S-fluoromethyl ester Example 13 was prepared from Intermediate 13 using a method analogous to that described for Example 1: LCMS retention time 3.92 min, m/z 633/635 MH$^+$

Example 14

17α-[(2,5-Dichlorothiophene-3-carbonyl)oxy]-6α,9α-difluoro-11β-hydroxy-16α-methyl-3-oxo-androsta-1,4-diene-17β-carbothioic acid S-fluoromethyl ester Example 14 was prepared from Intermediate 14 using a method analogous to that described for Example 1: LCMS retention time 4.17 min, m/z 623/625/627 MH$^+$

Example 15

17α-[(5-Bromofuran-2-carbonyl)oxy]-6α,9α-difluoro-11β-hydroxy-16α-methyl-3-oxo-androsta-1,4-diene-17β-carbothioic acid S-fluoromethyl ester Example 15 was prepared from Intermediate 15 using a method analogous to that described for Example 1: LCMS retention time 3.78 min, m/z 615/617 MH$^+$

Example 16

6α,9α-Difluoro-17α-[(2,5-dimethylfuran-3-carbonyl)oxy]-11β-hydroxy-16α-methyl-3-oxo-androsta-1,4-diene-17β-carbothioic acid S-fluoromethyl ester Example 16 was prepared from Intermediate 16 using a method analogous to that described for Example 1: LCMS retention time 3.85 min, m/z 576 MH$^+$

Example 17

17α-[(3-Chlorothiophene-2-carbonyl)oxy]-6α,9α-difluoro-11β-hydroxy-16α-methyl-3-oxo-androsta-1,4-diene-17β-carbothioic acid S-fluoromethyl ester Example 17 was prepared from Intermediate 17 using method analogous to that described for Example 1: LCMS retention time 3.88 min, m/z 589/591 MH$^+$

Example 18

6α,9α-Difluoro-11β-hydroxy-16α-methyl-17α-[(2-methylfuran-3-carbonyl)oxy]-3-oxo-androsta-1,4-diene-17β-carbothioic acid S-fluoromethyl ester Example 18 was prepared from Intermediate 18 using a method analogous to that described for Example 1: LCMS retention time 3.74 min, m/z 553 MH$^+$

Example 19

6α,9α-Difluoro-11β-hydroxy-16α-methyl-17α-[(3-methylfuran-2-carbonyl)oxy]-3-oxo-androsta-1,4-diene-17β-carbothioic acid S-fluoromethyl ester Example 19 was prepared from Intermediate 19 using a method analogous to that described for Example 1: LCMS retention time 3.66 min, m/z 553 MH$^+$

Example 20

6α,9α-Difluoro-11βhydroxy-16α-methyl-17α-[(5-methylisoxazole-4-carbonyl)oxy]-3-oxo-androsta-1,4-diene-17β-carbothioic acid S-fluoromethyl ester Example 20 was prepared from Intermediate 20 using a method analogous to that described for Example 1: LCMS retention time 3.60 min, m/z 554 MH$^+$

Example 21

6α,9α-Difluoro-11β-hydroxy-16α-methyl-17α-[(1-methyl-1H-pyrrole-2-carbonyl)oxy]-3-oxo-androsta-1,4-diene-17β-carbothioic acid S-fluoromethyl ester Example 21 was prepared from Intermediate 21 using a method analogous to that described for Example 1: LCMS retention time 3.72 min, m/z 552 MH$^+$

Example 22

6α,9α-Difluoro-11β-hydroxy-16α-methyl-3-oxo-17α-[(1,3-thiazole-4-carbonyl)oxy]-androsta-1,4-diene-17β-carbothioic acid S-fluoromethyl ester Example 22 was prepared from Intermediate 22 using a method analogous to that described for Example 1: LCMS retention time 3.47 min, m/z 552 MH$^+$

Example 23

6α,9α-Difluoro-17α-[(2,4-dimethyl-1,3-thiazole-5-carbonyl)oxy]-11β-hydroxy-16α-methyl-3-oxo-androsta-1,4-diene-17 β-carbothioic acid S-fluoromethyl ester Example 23 was prepared from Intermediate 23 using a method analogous to that described for Example 1: LCMS retention time 3.51 min, m/z 584 MH$^+$

Example 24

6α,9α-Difluoro-11β-hydroxy-16α-methyl-17α-[(5-methylisoxazole-3-carbonyl)oxy]-3-oxo-androsta-1,4-diene-17β-carbothioic acid S-fluoromethyl ester Example 24 was prepared from Intermediate 24 using a method analogous to that described for Example 1: LCMS retention time 3.65 min, m/z 554 MH$^+$

Example 25

6α,9α-Difluoro-11β-hydroxy-16α-methyl-17α-[(3-methylisoxazole-5-carbonyl)oxy]-3-oxo-androsta-1,4-diene-17β-carbothioic acid S-fluoromethyl ester Example 25 was prepared from Intermediate 25 using a method analogous to that described for Example 1: LCMS retention time 3.52 min, m/z 554 MH$^+$

Example 26

6α,9α-Difluoro-17α-[(1,3-dimethyl-1H-pyrazole-5-carbonyl)oxy]-11β-hydroxy-16α-methyl-3-oxo-androsta-1,4-diene-17β-carbothioic acid S-fluoromethyl ester Example 26 was prepared from Intermediate 26 using a method analogous to that described for Example 1: LCMS retention time 3.52 min, m/z 567 MH$^+$

Example 27

6α,9α-Difluoro-11β-hydroxy-16α-methyl-3-oxo-17α-[(1,2,3-thiadiazole-5-carbonyl)oxy]-androsta-1,4-diene-17β-carbothioic acid S-fluoromethyl ester Example 27 was prepared from Intermediate 27 using a method analogous to that described for Example 1: LCMS retention time 3.47 min, m/z 557 MH$^+$

Example 28

6α,9α-Difluoro-11β-hydroxy-17α-[(isoxazole-3-carbonyl)oxy]-16α-methyl-3-oxo-androsta-1,4-diene-17β-carbothioic acid S-fluoromethyl ester Example 28 was prepared from Intermediate 28 using a method analogous to that described for Example 1: LCMS retention time 3.48 min, m/z 540 MH$^+$

Example 29

6α,9α-Difluoro-11β-hydroxy-17α-[(4-methoxy-thiophene-3-carbonyl)oxy]-16α-methyl-3-oxo-androsta-1,4-diene-17β-carbothioic acid S-fluoromethyl ester Example 29 was prepared from Intermediate 29 using a method analogous to that described for Example 1: LCMS retention time 3.69 min, m/z 585 MH$^+$

Example 30

6α,9α-Difluoro-11β-hydroxy-16α-methyl-17α-[(2-methyl-1,3-thiazole-4-carbonyl)oxy]-3-oxo-androsta-1,4-diene-17β-carbothioic acid S-fluoromethyl ester Example 30 was prepared from Intermediate 30 using a method analogous to that described for Example 1: LCMS retention time 3.47 min, m/z 570 MH$^+$

Example 31

6α,9α-Difluoro-17α-[(3-ethoxy-thiophene-2-carbonyl)oxy]-11β-hydroxy-16α-methyl-3-oxo-androsta-1,4-diene-17β-carbothioic acid S-fluoromethyl ester Example 31 was prepared from Intermediate 31 using a method analogous to that described for Example 1: LCMS retention time 3.68 min, m/z 599 MH$^+$

Example 32

6α,9α-Difluoro-11β-hydroxy-16α-methyl-3-oxo-17α-[(1,2,3-thiadiazole-4-carbonyl)oxy]-androsta-1,4-diene-17β-carbothioic acid S-fluoromethyl ester Example 32 was prepared from Intermediate 32 using a method analogous to that described for Example 1: LCMS retention time 3.30 min, m/z 557 MH$^+$

Example 33

6α,9α-Difluoro-11β-hydroxy-16α-methyl-3-oxo-17α-[(1H-pyrrole-2-carbonyl)oxy]-androsta-1,4-diene-17β-carbothioic acid S-fluoromethyl ester Example 33 was prepared from Intermediate 33 using a method analogous to that described for Example 1: LCMS retention time 3.42 min, m/z 528 MH⁺

Example 34

6α,9α-Difluoro-11β-hydroxy-16α-methyl-3-oxo-17α-[(1,3-thiazole-5-carbonyl)oxy]-androsta-1,4-diene-17β-carbothioic acid S-fluoromethyl ester Example 34 was prepared from Intermediate 34 using a method analogous to that described for Example 1: LCMS retention time 3.44 min, m/z 556 MH⁺

Example 35

6α,9α-Difluoro-11β-hydroxy-16α-methyl-3-oxo-17α[(1,2,5-thiadiazole-3-carbonyl)oxy]-androsta-1,4-diene-17β-carbothioic acid S-fluoromethyl ester Example 35 was prepared from Intermediate 35 using a method analogous to that described for Example 1: LCMS retention time 3.53 min, m/z 557 MH⁺

Example 36

6α,9α-Difluoro-11β-hydroxy-17α-[(isothiazole-3-carbonyl)oxy]-16α-methyl-3-oxo-androsta-1,4-diene-17β-carbothioic acid S-fluoromethyl ester Example 36 was prepared from Intermediate 36 using a method analogous to that described for Example 1: LCMS retention time 3.51 min, m/z 556 MH⁺

Example 37

6α,9α-Difluoro-11β-hydroxy-17α-[(isothiazole-5-carbonyl)oxy]-16α-methyl-3-oxo-androsta-1,4-diene-17β-carbothioic acid S-fluoromethyl ester Example 37 was prepared from Intermediate 37 using a method analogous to that described for Example 1: LCMS retention time 3.59 min, m/z 556 MH⁺

Example 38

6α,9α-Difluoro-11β-hydroxy-16α-methyl-17α-[(5-methylthiophene-2-carbonyl)oxy]-3-oxo-androsta-1,4-diene-17β-carbothioic acid S-fluoromethyl ester Example 38 was prepared from Intermediate 7 using a method analogous to that described for Example 1: LCMS retention time 3.78 min, m/z 569 MH⁺

Example 39

6α,9α-Difluoro-17α-[(2-furanylcarbonyl)oxy]-11β-hydroxy-16α-methyl -3-oxo-androsta-1,4-diene-17β-carbothioic acid S-methyl ester A suspension of Intermediate 1 (507 mg, 1 mmol) was dissolved in anhydrous N,N-dimethylformamide (5 ml) and sodium hydrogen carbonate (92 mg, 1.1 mmol) was added. The mixture was stirred at 0° C. and iodomethane (0.125 ml, 2 mmol) was added and the mixture was stirred at 0–5° C. for 2.5 h. Diethylamine (0.41 ml, 4 mmole) was added and the mixture stirred at 5° C. for 30 min. The mixture was added to 2M hydrochloric acid (25 ml) to give a white precipitate. Water (75 ml) was added and the precipitate was collected by filtration to give the title compound as a white solid (456 mg, 88%): LCMS retention time 3.54 min, m/z 521 MH⁺.

Example 40

6α,9α-Difluoro-11β-hydroxy-16α-methyl-17α-[(3-methylthiophene-2-carbonyl)oxy]-3-oxo-androsta-1,4-diene-17β-carbothioic acid S-fluoromethyl ester Example 40 was prepared from Intermediate 38 using a method analogous to that described for Example 1: LCMS retention time 3.78 min, m/z 569 MH⁺

Example 41

6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester Example 41 was prepared from Intermediate 39 using a method analogous to that described for Example 1: LCMS retention time 3.51 min, m/z 570 MH⁺

Example 42

17α-[(1-Ethyl-3-methyl-1H-pyrazole-5-carbonyl)oxy]-6α,9α-difluoro-11β-hydroxy-16α-methyl-3-oxo-androsta-1,4-diene-17β-carbothioic acid S-fluoromethyl ester Example 42 was prepared from Intermediate 40 using a method analogous to that described for Example 1: LCMS retention time 3.64 min, m/z 581 MH⁺

Example 43

6α,9α-Difluoro-17α-[(1-methyl-1H-imidazole-5-carbonyl)oxy]-11β-hydroxy-16α-methyl-3-oxo-androsta-1,4-diene-17β-carbothioic acid S-fluoromethyl ester Example 43 was prepared from Intermediate 41 using a method analogous to that described for Example 1: LCMS retention time 3.14 min, m/z 553 MH⁺

Example 44

Dry Powder Composition Containing 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester A dry powder formulation may be prepared as follows:

| | |
|---|---|
| 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester (prepared according to Example 41 and micronised to a MMD of 3 µm): | 0.20 mg |
| milled lactose (wherein not greater than 85% of particles have a MMD of 60–90 µm, and not less than 15% of particles have a MMD of less than 15 µm): | 12 mg |

A peelable blister strip containing 60 blisters each filled with a formulation as just described may be prepared.

Example 45

Dry Powder Composition Containing 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and a Long Acting β₂-adrenoreceptor Agonist A dry powder formulation may be prepared as follows:

| | |
|---|---|
| 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester (prepared according to Example 41 and micronised to a MMD of 3 μm): | 0.20 mg |
| Long-acting β₂-adrenoreceptor agonist (micronised to a MMD of 3 μm): | 0.02 mg |
| milled lactose (wherein not greater than 85% of particles have a MMD of 60–90 μm, and not less than 15% of particles have a MMD of less than 15 μm): | 12 mg |

A peelable blister strip containing 60 blisters each filled with a formulation as just described may be prepared.

Example 46

Aerosol Formulation Containing 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester An aluminium canister may be filled with a formulation as follows:

| | |
|---|---|
| 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester (prepared according to Example 41 and micronised to a MMD of 3 μm): | 250 μg |
| 1,1,1,2-tetrafluoroethane: | to 50 μl |

(amounts per actuation)
in a total amount suitable for 120 actuations and the canister may be fitted with a metering valve adapted to dispense 50 μl per actuation.

Example 47

Aerosol Formulation Containing 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and a Long Acting β₂-adrenoreceptor Agonist An aluminium canister may be filled with a formulation as follows:

| | |
|---|---|
| 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester (prepared according to Example 41 and micronised to a MMD of 3 μm): | 250 μg |
| Long-acting β₂-adrenoreceptor agonist (micronised to a MMD of 3 μm): | 25 μg |
| 1,1,1,2-tetrafluoroethane: | to 50 μl |

(amounts per actuation)
in a total amount suitable for 120 actuations and the canister may be fitted with a metering valve adapted to dispense 50 μl per actuation.

Example 49

Nasal Formulation Containing 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester A formulation for intranasal delivery may be prepared as follows:

| | |
|---|---|
| 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester (prepared according to Example 41, micronised): | 10 mg |
| Polysorbate 20 | 0.8 mg |
| Sorbitan monolaurate | 0.09 mg |
| Sodium dihydrogen phosphate dihydrate | 94 mg |
| Dibasic sodium phosphate anhydrous | 17.5 mg |
| Sodium chloride | 48 mg |
| Demineralised water | to 10 ml |

The formulation may be fitted into a spraypump capable of delivering a plurality of metered doses (Valois).

Pharmacological Activity

In Vitro Pharmacological Activity

Pharmacological activity was assessed in a functional in vitro assay of glucocorticoid agonist activity which is generally predictive of anti-inflammatory or anti-allergic activity in vivo.

The functional assay was based on that described by K. P. Ray et al., Biochem J. (1997), 328, 707–715. A549 cells stably transfected with a reporter gene containing the NF-κB responsive elements from the ELAM gene promoter coupled to sPAP (secreted alkaline phosphatase) were treated with test compounds at appropriate doses for 1 hour at 37° C. The cells were then stimulated with tumour necrosis factor (TNF, 10 ng/ml) for 16 hours, at which time the amount of alkaline phosphatase produced is measured by a standard colourimetric assay. Dose response curves were constructed from which $EC_{50}$ values were estimated.

In this test the compounds of Examples 1 to 9, 11–13, 15–22 and 24–42 showed an $EC_{50}$ value of <1 nM. In this test the compounds of Examples 10, 14 and 23 showed an EC50 value of 1, 2 and 17 nM respectively.

The glucocorticoid receptor (GR) can function in at least two distinct mechanisms, by upregulating gene expression through the direct binding of GR to specific sequences in gene promoters, and by downregulating gene expression that is being driven by other transcription factors (such as NFκB or AP-1) through their direct interaction with GR.

In a variant of the above method, to monitor these functions, two reporter plasmids have been generated and introduced separately into A549 human lung epithelial cells by transfection. The first cell line contains the firefly luciferase reporter gene under the control of a synthetic promoter that specifically responds to activation of the transcription factor NFκB when stimulated with TNFα. The second cell line contains the renilla luciferase reporter gene under the control of a synthetic promotor that comprises 3 copies of the consensus glucocorticoid response element, and which responds to direct stimulation by glucocorticoids. Simultaneous measurement of transactivation and transrepression was conducted by mixing the two cell lines in a 1:1 ratio in 96 well plate (40,000 cells per well) and growing overnight at 37° C. Test compounds were dissolved in DMSO, and added to the cells at a final DMSO concentration of 0.7%. After incubation for 1 h 0.5 ng/ml TNFα (R&D Systems) was added and after a further 15 hours at 37° C., the levels of firefly and renilla luciferase were measured using the Packard Firelite kit following the manufacturers' directions. Dose response curves were constructed from which $EC_{50}$ values were determined.

|  | Transactivation (GR) $ED_{50}$ (nM) | Transrepression (NFκB) $ED_{50}$ (nM) |
|---|---|---|
| Example 1 | 0.06 | 0.20 |
| Metabolite (X) | >250 | >1000 |
| Fluticasone propionate | 0.07 | 0.16 |

Screen for Progesterone Receptor Activity

The human breast cancer cell line T47D has been reported to upregulate an endogenous alkaline phosphatase in response to progestins (Di Lorenzo et al., Cancer Research (1991) 51, 4470–4475. T47D cells were seeded into 96 well plates at a density of 1×10$^5$ cells per well and grown overnight at 37° C. Steroids were dissolved in DMSO, added to the cells (final DMSO concentration 0.7%), and incubated for 24 hours at 37° C. The cells were then washed with PBS and lysed with RIPA buffer (1% IGEPAL, 0.5% Na deoxycholate, 0.1% SDS in phosphate buffered saline). Alkaline phosphatase activity was measured spectrophotometrically (405 nm) using p-nitrophenylphosphate (1.5 mg/ml) as a substrate dissolved in 1M diethanolamine, 0.28M NaCl, 0.5 mM MgCl$_2$. Dose response curves were constructed from which $EC_{50}$ values were estimated.

Examples 12 and 41 were tested for progesterone activity in accordance with the above screen and the selectivity was determined by dividing the $ED_{50}$ at the progesterone receptor by the $ED_{50}$ at the glucocorticoid receptor.

The selectivity of Example 12 was determined to be 364 (compare fluticasone propionate: selectivity=23)

In separate experiment, the selectivity of Example 41 was determined to be 1599 (compare fluticasone propionate: selectivity=60)

In Vivo Pharmacological Activity

Pharmacological activity in vivo was assessed in an ovalbumin sensitised Brown Norway rat eosinophilia model. This model is designed to mimic allergen induced lung eosinophilia, a major component of lung inflammation in asthma.

Example 1 produced dose dependant inhibition of lung eosinophilia in this model after dosing as an intra-tracheal (IT) suspension in saline 30 min prior to ovalbumin challenge. Significant inhibition is achieved after a single dose of 30 μg of Example 1 and the response was significantly (p=0.016) greater than that seen with an equivalent dose of fluticasone propionate in the same study (69% inhibition with Example 1 vs 41% inhibition with fluticasone propionate).

In a rat model of thymus involution 3 daily IT doses of 100 μg of Example 1 induced significantly smaller reductions in thymus weight (p=0.004) than an equivalent dose of fluticasone propionate in the same study (67% reduction of thymus weight with Example 1 vs 78% reduction with fluticasone propionate).

Taken together these results indicate a superior therapeutic index for Example 1 compared to fluticasone propionate.

In vitro Metabolism in Rat and Human Hepatocytes

Incubation of Example 1 with rat or human hepatocytes shows the compound to be metabolised in an identical manner to fluticasone propionate with the 17-β carboxylic acid (X) being the only significant metabolite produced. Investigation of the rate of appearance of this metabolite on incubation of Example 1 with human hepatocytes (37° C., 10 μM drug concentration, hepatocytes from 3 subjects, 0.2 and 0.7 million cells/mL) shows Example 1 to be metabolised ca. 5-fold more rapidly than fluticasone propionate:

| Subject number | Cell density (million cells/mL) | 17-β acid metabolite production (pmol/h) | |
|---|---|---|---|
|  |  | Example 1 | Fluticasone propionate |
| 1 | 0.2 | 48.9 | 18.8 |
| 1 | 0.7 | 73.3 | 35.4 |
| 2 | 0.2 | 118 | 9.7 |
| 2 | 0.7 | 903 | 23.7 |
| 3 | 0.2 | 102 | 6.6 |
| 3 | 0.7 | 580 | 23.9 |

Median metabolite production 102-118 pmol/h for Example 1 and 18.8-23.0 pmol/h for fluticasone propionate.

Pharmacokinetics After Intravenous (IV) and Oral Dosing in Rats

Examples 1 and 41 were dosed orally (0.1 mg/kg) and IV (0.1 mg/kg) to male Wistar Han rats and pharmacokinetic parameters determined. Example 1 showed negligible oral bioavailability (0.9%) and plasma clearance of 47.3 mL/min/kg, approaching liver blood flow (plasma clearance of fluticasone propionate=45.2 mL/min/kg).

Examples 4, 19, 24, 25, 28 and 41 were dosed IV (0.1 mg/kg) to male Wistar Han rats and plasma clearance values of 49, 48, 47, 46, 51 and 42 mL/min/kg respectively were determined.

Pharmacokinetics After Intra-tracheal Dry Powder Dosing in the Pig

Anaesthetised pigs (2) were dosed intra-tracheally with a homogenous mixture of Example 1 (1 mg) and fluticasone propionate (1 mg) as a dry powder blend in lactose (10% w/w). Serial blood samples were taken for up to 8 h following dosing. Plasma levels of Example 1 and fluticasone propionate were determined following extraction and analysis using LC-MS/MS methodology, the lower limits of quantitation of the methods were 10 and 20 pg/mL for Example 1 and fluticasone propionate respectively. Using these methods Example 1 was quantifiable up to 2 hours after dosing and fluticasone propionate was quantifiable up to 8 hours after dosing. Maximum plasma concentrations were observed for both compounds within 15 min after dosing. Plasma half-life data obtained from IV dosing (0.1 mg/kg) was used to calculate AUC (0-inf) values for Example 1. This compensates for the plasma profile of Example 1 only being defined up to 2 hours after an IT dose and removes any bias due to limited data between Example 1 and fluticasone propionate.

$C_{max}$ and AUC (0-inf) values show markedly reduced systemic exposure to Example 1 compared to fluticasone propionate:

|  | Cmax (pg/mL) | | AUC (0-inf) (hr.pg/mL) | |
|---|---|---|---|---|
|  | Pig 1 | Pig 2 | Pig 1 | Pig 2 |
| Example 1 | 117 | 81 | 254 | 221 |
| Fluticasone propionate | 277 | 218 | 455 | 495 |

The pharmacokinetic parameters for both Example 1 and fluticasone propionate were the same in the anaesthetised pig following intravenous administration of a mixture of the two compounds at 0.1 mg/kg. The clearance of these two glucocortocoids is similar is this experimental pig model.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The patents and patent applications described in this application are herein incorporated by reference.

What is claimed is:

1. A method of treatment of COPD comprising the administration by inhalation of a pharmaceutical formulation comprising a compound of formula (I),

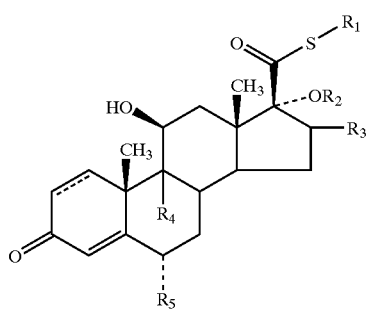

wherein $R_1$ represents $C_{1-6}$ alkyl or $C_{1-6}$ haloalkyl;

$R_2$ represents —C(=O)-aryl or —C(=O)-heteroaryl;

$R_3$ represents hydrogen, methyl (which may be in either the α or β configuration) or methylene;

$R_4$ and $R_5$ are the same or different and each represents hydrogen or halogen; and === represents a single or a double bond;

or a salt or solvate thereof, together with a long-acting $\beta_2$-adrenoreceptor agonist wherein said formulation has a therapeutically useful effect in the treatment of COPD over a period of 24 hours or more.

2. The method of treatment claim 1, wherein the compound of formula (I) or a solvate thereof and the long-acting $\beta_2$-adrenoreceptor agonist are both present in particulate form.

3. The method of treatment claim 2, wherein said pharmaceutical formulation further comprising a particulate carrier.

4. The method treatment of claim 3, wherein the carrier in said pharmaceutical formulation is lactose.

5. The method of treatment of claim 1, wherein said pharmaceutical formulation further comprises a liquified propellant gas.

6. The method of treatment of claim 2, wherein said pharmaceutical formulation further comprises a liquified propellant gas.

7. A method of treatment of COPD over a period of 24 hours, or more, comprising delivering to a patient one or more doses once-per-day from an inhaler containing a plurality of doses of a pharmaceutical formulation comprising a compound of formula (I)

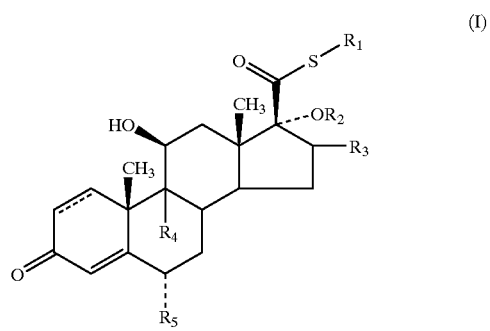

wherein $R_1$ represents $C_{1-6}$ alkyl or $C_{1-6}$ haloalkyl;

$R_2$ represents —C(=O)-aryl or —C(=O)-heteroaryl;

$R_3$ represents hydrogen, methyl (which may be in either the α or β configuration) or methylene;

$R_4$ and $R_5$ are the same or different and each represents hydrogen or halogen; and === represents a single or a double bond;

or a salt or solvate thereof, together with a long-acting $\beta_2$-adrenoreceptor agonist which formulation has a therapeutically useful effect in the treatment of COPD over a period of 24 hours or more, and which doses are suitable for once-per-day administration of the formulation by inhalation.

8. The method of treatment of claim 7, wherein the compound of formula (I) or a solvate thereof and the long-acting $\beta_2$-adrenoreceptor agonist are both present in particulate form.

9. The method of treatment of claim 8, wherein the formulation further comprises a particulate carrier.

10. The method of treatment of claim 9, wherein the carrier is lactose.

11. The method of treatment of claim 7, wherein the formulation further comprises a liquefied propellant gas.

12. The method of treatment of claim 8, wherein the formulation further comprises a liquefied propellant gas.

13. A method of treatment of COPD by inhalation comprising administering by once-per-day dosing from an inhaler containig a plurality of doses of a pharmaceutical formulation comprising a particulate compound of formula (I)

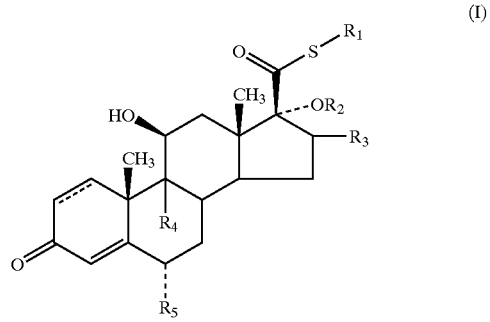

wherein $R_1$ represents $C_{1-6}$ alkyl or $C_{1-6}$ haloalkyl;

$R_2$ represents —C(=O)-aryl or —C(=O)-heteroaryl;

$R_3$ represents hydrogen, methyl (which may be in either the α or β configuration) or methylene;

$R_4$ and $R_5$ are the same or different and each represents hydrogen or halogen; and ═══ represents a single or a double bond;

or a salt or solvate thereof, together with a long-acting $\beta_2$-adrenoreceptor, a particulate long-acting $\beta_2$-adrenoreceptor agonist and a carrier each drug being present in an amount adequate to provide a therapeutically useful effect in the treatment of COPD over a period of 24 hours or more following once-per-day dosing by inhalation.

14. The method of treatment of claim 1, wherein the compound of formula (I) is 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester or a salt or solvate thereof.

15. The method of treatment of claim 2 wherein the compound of formula (I) is 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester or a salt or solvate thereof.

16. The method of treatment of claim 3 wherein the compound of formula (I) is 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester or a salt or solvate thereof.

17. The method of treatment of claim 4 wherein the compound of formula (I) is 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester or a salt or solvate thereof.

18. The method of treatment of claim 5 wherein the compound of formula (I) is 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester or a salt or solvate thereof.

19. The method of treatment of claim 6 wherein the compound of formula (I) is 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester or a salt or solvate thereof.

20. The method of treatment of claim 7 wherein the compound of formula (I) is 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester or a salt or solvate thereof.

21. The method of treatment of claim 8 wherein the compound of formula (I) is 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester or a salt or solvate thereof.

22. The method of treatment of claim 9 wherein the compound of formula (I) is 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester or a salt or solvate thereof.

23. The method of treatment of claim 10 wherein the compound of formula (I) is 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester or a salt or solvate thereof.

24. The method of treatment of claim 11 wherein the compound of formula (I) is 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester or a salt or solvate thereof.

25. The method of treatment of claim 12 wherein the compound of formula (I) is 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester or a salt or solvate thereof.

26. The method of treatment of claim 13 wherein the compound of formula (I) is 6α,9α-Difluoro-11β-hydroxy-16α-methyl-17β-[(4-methyl-1,3-thiazole-5-carbonyl)oxy]-3-oxo-androsta-1,4-diene-17β-carbothioic acid S-fluoromethyl ester or a salt or solvate thereof.

27. The method of treatment of claim 1, in which $R_1$ represents fluoromethyl, chloromethyl, bromomethyl or 2'-fluoroethyl.

28. The method of treatment of claim 27, in which $R_1$ represents fluoromethyl.

29. The method of treatment of claim 1, in which $R_2$ represents —C(═O)-heteroaryl.

30. The method of treatment of claim 29, wherein heteroaryl represents a 5-membered heterocyclic aromatic ring containing 1 to 3 heteroatoms selected from O, N and S which may optionally be substituted.

31. The method of treatment of claim 30, wherein the heterocyclic ring is substituted with one or more substituents selected from $C_{1-6}$alkyl, $C_{1-6}$alkoxy and halogen.

32. The method of treatment of claim 30, in which the heterocyclic ring is furanyl, pyrrolyl or thiophenyl.

33. The method of treatment of claim 32, in which the heterocyclic ring is furanyl or thiophenyl.

34. The method of treatment of claim 30, in which the 5-membered heterocyclic ring contains 2 heteroatoms selected from O, N and S.

35. The method of treatment of claim 24, wherein the heterocyclic ring is selected from thiazolyl, isothiazolyl, pyrazolyl and imidazolyl.

36. The method of treatment of claim 30, in which the 5-membered heterocyclic ring contains 3 heteroatoms selected from O, N and S.

37. The method of treatment of claim 36, wherein the heterocycle is thiadiazolyl.

38. The method of treatment of claim 32, wherein the heterocyclic ring is substituted with one or more substituents selected from $C_{1-6}$alkyl and halogen.

39. The method of treatment of claim 1, in which $R_3$ is methyl.

40. The method of treatment of claim 1, in which $R_4$ and $R_5$ are the same or different and each represents hydrogen, fluorine or chlorine.

41. The method of treatment of claim 1, in which $R_4$ and $R_5$ are the same or different and each represents hydrogen or fluorine.

42. The method of treatment of claim 1, in which both $R_4$ and $R_5$ are fluorine.

43. The method of treatment of claim 1, in which $R_1$ is fluoromethyl; $R_2$ is —C(═O)-2-furanyl; $R_3$ is methyl; $R_4$ and $R_5$ are the same or different and each represents hydrogen or fluorine; and ═══ represents a single or a double bond.

44. The method of treatment of claim 43, in which $R_4$ and $R_5$ are each fluorine.

45. The method of treatment of claim 1, in which ═══ represents a double bond.

46. The method of treatment of claim 1, wherein the compound of formula (I) is:

6α,9α-Difluoro-17α-[(3-furanylcarbonyl)oxy]-11β-hydroxy-16α-methyl-3-oxo-androsta-1,4-diene-17β-carbothioic acid S-fluoromethyl ester;

6α,9α-Difluoro-11β-hydroxy-16α-methyl-3-oxo-17α-[(2-thienylcarbonyl)oxy]-androsta-1,4-diene-17β-carbothioic acid S-fluoromethyl ester;

6α,9α-Difluoro-11β-hydroxy-16α-methyl-3-oxo-17α-[(3-thienylcarbonyl)oxy]-androsta-1,4-diene-17β-carbothioic acid S-fluoromethyl ester;

17α-(Benzoyl)oxy-6α,9α-Difluoro-11β-hydroxy-16α-methyl-3-oxo-androsta-1,4-diene-17β-carbothioic acid S-fluoromethyl ester;

9α-Fluoro-17α-[(2-furanylcarbonyl)oxy]-11β-hydoxy-16β-methyl-3-oxo-androsta-1,4-diene-17β-carbothioic acid S-fluoromethyl ester;

6α,9α-Difluoro-17α-[(2-furanylcarbonyl)oxy]-11β-hydoxy-16α-methyl-3-oxo-androst-4-ene-17β-carbothioic acid S-fluoromethyl ester;

or a salt or solvate of any one thereof.

47. The method of treatment of claim 1, wherein the compound of formula (I) is:

6α,9α-Difluoro-11β-hydroxy-17α-[(isoxazole-5-cabonyl)oxy]-16α-methyl-3-oxo-androsta-1,4-diene-17β-carbothioic acid S-fluoromethyl ester;

17α-[(5-Chlorothiophene-2-carbonyl)oxy]-6α,9α-difluoro-11β-hydroxy-16α-methyl-3-oxo-androsta-1,4-diene-17β-carbothioic acid S-fluoromethyl ester;

6α,9α-Difluoro-17α-[(3,5-dimethylisoxazole-4-carbonyl)oxy]-11β-hydroxy-16α-methyl-3-oxo-androsta-1,4-diene-17β-carbothioic acid S-fluoromethyl ester;

17α-[(5-Chloro-4-methoxy-thiophene-3-carbonyl)oxy]-6α,9α-difluoro-11β-hydroxy-16α-methyl-3-oxo-androsta-1,4-diene-17β-carbothioic acid S-fluoromethyl ester;

6α,9α-Difluoro-11β-hydroxy-16α-methyl-17α-[(4-methyl-1,2,3-thiadiazole-5-carbonyl)oxy]-3-oxo-androsta-1,4-diene-17β-carbothioic acid S-fluoromethyl ester;

17α-[(3-Bromothiophene-2-carbonyl)oxy]-6α,9α-difluoro-11β-hydroxy-16α-methyl-3-oxo-androsta-1,4-diene-17β-carbothioic acid S-fluoromethyl ester;

17α-[(2,5-Dichlorothiophene-3-carbonyl)oxy]-6α,9α-difluoro-11β-hydroxy-16α-methyl-3-oxo-androsta-1,4-diene-17β-carbothioic acid S-fluoromethyl ester;

17α[(5-Bromofuran-2-carbonyl)oxy]-6α,9α-difluoro-11β-hydroxy-16α-methyl-3-oxo-androsta-1,4-diene-17β-carbothioic acid S-fluoromethyl ester;

6α,9α-Difluoro-17α-[(2,5-dimethylfuran-3-carbonyl)oxy]-11β-hydroxy-16α-methyl-3-oxo-androsta-1,4-diene-17β-carbothioic acid S-fluoromethyl ester;

17α-[(3-Chlorothiophene-2-carbonyl)oxy]-6α,9α-difluoro-11β-hydroxy-16α-methyl-3-oxo-androsta-1,4-diene-17β-carbothioic acid S-fluoromethyl ester;

6α,9α-Difluoro-11β-hydroxy-16α-methyl-17α-[(2-methylfuran-3-carbonyl)oxy]-3-oxo-androsta-1,4-diene-17β-carbothioic acid S-fluoromethyl ester;

6α,9α-Difluoro-11β-hydroxy-16α-methyl-17α-[(3-methylfuran-2-carbonyl)oxy]-3-oxo-androsta-1,4-diene-17β-carbothioic acid S-fluoromethyl ester;

6α,9α-Difluoro-11β-hydroxy-16α-methyl-17α-[(5-methylisoxazole-4-carbonyl)oxy]-3-oxo-androsta-1,4-diene-17β-carbothioic acid S-fluoromethyl ester;

6α,9α-Difluoro-11β-hydroxy-16α-methyl-17α-[(1-methyl-1H-pyrrole-2-carbonyl)oxy]-3-oxo-androsta-1,4-diene-17β-carbothioic acid S-fluoromethyl ester;

6α,9α-Difluoro-11β-hydroxy-16α-methyl-3-oxo-17α-[(1,3-thiazole-4-carbonyl)oxy]-androsta-1,4-diene-17β-carbothioic acid S-fluoromethyl ester;

6α,9α-Difluoro-17α-[(2,4-dimethyl-1,3-thiazole-5-carbonyl)oxy]-11β-hydroxy-16α-methyl-3-oxo-androsta-1,4-diene-17β-carbothioic acid S-fluoromethyl ester;

6α,9α-Difluoro-11β-hydroxy-16α-methyl-17α-[(5-methylisoxazole-3-carbonyl)oxy]-3-oxo-androsta-1,4-diene-17β-carbothioic acid S-fluoromethyl ester;

6α,9α-Difluoro-11β-hydroxy-16α-methyl-17α-[(3-methylisoxazole-5-carbonyl)oxy]-3-oxo-androsta-1,4-diene-17β-carbothioic acid S-fluoromethyl ester;

6α,9α-Difluoro-17α-[(1,3-dimethyl-1H-pyrazole-5-carbonyl)oxy]-11β-hydroxy-16α-methyl-3-oxo-androsta-1,4-diene-17β-carbothioic acid S-fluoromethyl ester;

6α,9α-Difluoro-11β-hydroxy-17α-[(isoxazole-3-carbonyl)oxy]-16α-methyl-3-oxo-androsta-1,4-diene-17α-carbothioic acid S-fluoromethyl ester;

6α,9α-Difluoro-11β-hydroxy-17α-[(4-methoxy-thiophene-3-carbonyl)oxy]-16α-methyl-3-oxo-androsta-1,4-diene-17β-carbothioic acid S-fluoromethyl ester;

6α,9α-Difluoro-11β-hydroxy-16α-methyl-17α-[(2-methyl-1,3-thiazole-4-carbonyl)oxy]-3-oxo-androsta-1,4-diene-17β-carbothioic acid S-fluoromethyl ester;

6α,9α-Difluoro-17α-[(3-ethoxy-thiophene-2-carbonyl)oxy]-11β-hydroxy-16α-methyl-3-oxo-androsta-1,4-diene-17β-carbothioic acid S-fluoremethyl ester;

6α,9α-Difluoro-11β-hydroxy-16α-methyl-3-oxo-17α-[(1,2,3-thiadiazole-4-carbonyl)oxy]-androsta-1,4-diene-17β-carbothioic acid S-fluoromethyl ester;

6α,9α-Difluoro-11β-hydroxy-16α-methyl-3-oxo-17α-[(1H-pyrrole-2-carbonyl)oxy]-androsta-1,4-diene-17β-carbothioic acid S-fluoromethyl ester;

6α,9α-Difluoro-11β-hydroxy-16α-methyl-3-oxo-17α-[(1,3-thiazole-5-carbonyl)oxy]-androsta-1,4-diene-17β-carbothioic acid S-fluoromethyl ester;

6α,9α-Difluoro-11β-hydroxy-16α-methyl-3-oxo-17α-[(1,2,5-thiadiazole-3-carbonyl)oxy]-androsta-1,4-diene-17β-carbothioic acid S-fluoromethyl ester;

6α,9α-Difluoro-11β-hydroxy-17α-[(isothiazole-3-carbonyl)oxy]-16α-methyl-3-oxo-androsta-1,4-diene-17β-carbothioic acid S-fluoromethyl ester;

6α,9α-Difluoro-11β-hydroxy-17α-[(isothiazole-5-carbonyl)oxy]-16α-methyl-3-oxo-androsta-1,4-diene-17β-carbothioic acid S-fluoromethyl ester;

6α,9α-Difluoro-11β-hydroxy-16α-methyl-17α-[(5-methylthiophene-2-carbonyl)oxy]-3-oxo-androsta-1,4-diene-17β-carbothioic acid S-fluoromethyl ester;

6α,9α-Difluoro-17α-[(2-furanylcarbonyl)oxy]-11β-hydroxy-16α-methyl-3-oxo-androsta-1,4-diene-17β-carbothioic acid S-methyl ester;

6α,9α-Difluoro-11β-hydroxy-16α-methyl-17α-[(3-methylthiophene-2-carbonyl)oxy]-3-oxo-androsta-1,4-diene-17β-carbothioic acid S-fluoromethyl ester;

6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester;

17α-[(1-Ethyl-3-methyl-1H-pyrazole-5-carbonyl)oxy]-6α,9α-difluoro-11β-hydroxy-16α-methyl-3-oxo-androsta-1,4-diene-17β-carbothioic acid S-fluoromethyl ester;

6α,9α-Difluoro-17α-[(1-methyl-1H-imidazole-5-carbonyl)oxy]-11β-hydroxy-16α-methyl-3-oxo-androsta-1,4-diene-17β-carbothioic acid S-fluoromethyl ester;

6α,9α-Difluoro-11β-hydroxy-16α-methyl3-oxo-17α-[(1,2,3-thiadiazole-5-carbonyl)oxy]-androsta-1,4-diene-17β-carbothioic acid S-fluoromethyl ester;

or a salt or solvate of any one thereof.

48. The method of treatment of claim 1, wherein the method is for veterinary medicine.

49. The method of treatment of claim 1, wherein the method is for human medicine.

50. The method of treatment of claim 1, wherein the compound of formula (I) or a salt or solvate thereof is together, if desirable, in admixture with one or more physiologically acceptable diluents or carriers.

51. The method of treatment of claim 1, wherein the pharmaceutical formulation further comprises a fluorocarbon or hydrogen-containing chlorofluoro carbon as propellant, optionally in combination with a surfactant and or a cosolvent.

52. The method of treatment of claim 1, wherein in the compound of formula (I), $R_1$ represents $C_{1-6}$ alkyl; $R_2$ represents —C(=O)-aryl; $R_3$ represents hydrogen, methyl (which may be in either the α or β configuration) or methylene; $R_4$ and $R_5$ are the same or different and each represents hydrogen or halogen, and === represents a single or a double bond; or salts and solvates thereof.

53. The method of treatment of claim 52, wherein in the compound of formula (I), $R_3$ represents methyl (which may be in either the α or β configuration); $R_4$ and $R_5$ are the same or different and each represents halogen; and === represents a single or a double bond; or salts and solvates thereof.

54. The method of treatment of claim 52, wherein $R_3$ is methyl.

55. The method of treatment of claim 52, wherein $R_4$ and $R_5$ are the same or different and each represents hydrogen, fluorine or chlorine.

56. The method of treatment of claim 52, wherein $R_4$ and $R_5$ are the same or different and each represents hydrogen or fluorine.

57. The method of treatment of claim 52, wherein both $R_4$ and $R_5$ are fluorine.

58. The method of treatment of claim 52, wherein === represents a double bond.

59. The method of treatment of claim 52, wherein the method is for veterinary medicine.

60. The method of treatment of claim 52, wherein the method is for human medicine.

61. The method of treatment of claim 52, wherein the compound of formula (I) or a salt or solvate thereof is together, if desirable, in admixture with one or more physiologically acceptable diluents or carriers.

62. The method of treatment of claim 52, wherein the pharmaceutical formulation further comprises a fluorocarbon or hydrogen-containing chlorofluoro carbon as propellant, optionally in combination with a surfactant and/or a cosolvent.

63. The method of treatment of claim 61, wherein the composition is a dry powder or spray.

64. The method of treatment of claim 63, wherein the composition is a dry powder.

65. The method of treatment of claim 63, wherein the composition is a spray.

66. The method of treatment of claim 1, wherein the $β_2$-adrenoreceptor agonist is at least one selected from the group consisting of salmeterol, salbutamol, formoterol, salmefamol, fenoterol, terbutaline and salts thereof.

67. The method of treatment of claim 52, wherein the $β_2$-adrenoreceptor agonist is at least one selected from the group consisting of salmeterol, salbutamol, formoterol, salmefamol, fenoterol, terbutaline and salts thereof.

68. The method of treatment of claim 1, wherein said compound of formula (I) has a particle size in the range of 1–10 μm.

69. The method of treatment of claim 52, wherein said compound of formula (I) has a particle size in the range of 1–10 μm.

70. The method of treatment of claim 52, wherein the compound of formula (I) or a solvate thereof and the long-acting $β_2$-adrenoreceptor agonist are both present in particulate form.

71. The method of treatment of claim 70, wherein said pharmaceutical formulation further comprising a particulate carrier.

72. The method of treatment of claim 71, wherein the carrier in said pharmaceutical formulation is lactose.

73. The method of treatment of claim 52, wherein said pharmaceutical formulation further comprises a liquified propellant gas.

74. The method of treatment of claim 70, wherein said pharmaceutical formulation further comprises a liquified propellant gas.

75. The method of treatment of claim 1, wherein $R_1$ represents $C_{1-6}$ haloalkyl; $R_2$ represents —C(=O)-heteroaryl; $R_3$ represents hydrogen, methyl (which may be in either the α or β configuration) or methylene; $R_4$ and $R_5$ are the same or different and each represents hydrogen or halogen; and === represents a single or a double bond; or salts and solvates thereof.

76. The method of treatment of claim 75, wherein $R_3$ represents methyl (which may be in either the α or β configuration); $R_4$ and $R_5$ are the same or different and each represents halogen; and === represents a single or a double bond; or salts and solvates thereof.

77. The method of treatment of claim 75, wherein $R_1$ represents fluoromethyl, chloromethyl, bromomethyl or 2'-fluoromethyl.

78. The method of treatment of claim 75, wherein $R_1$ represents fluoromethyl.

79. The method of treatment of claim 75, wherein the heteroaryl of $R_2$ represents a 5-membered heterocyclic aromatic ring containing 1 to 3 heteroatoms and each of said 1–3 heteroatoms is independently selected from the group consisting of O, N and S which may optionlly be substituted.

80. The method of treatment of claim 79, wherein the 5-membered heterocyclic aromatic ring is substituted with one or more substituents selected from the group consisting of $C_{1-6}$alkyl, $C_{1-6}$alkoxy and halogen.

81. The method of treatment of claim 80, wherein the 5-membered heterocylic aromatic ring is selected from the group consisting of furanyl, pyrrolyl and thiophenyl.

82. The method of treatment of claim 81, wherein the 5-membered heterocyclic ring is furanyl or thiophenyl.

83. The method of treatment of claim 79, wherein the 5-membered heterocyclic ring contains 2 heteroatoms and each of said 2 heteroatoms is independently selected from the group cousisting of O, N and S.

84. The method of treatment of claim 79, wherein the 5-membered heterocyclic ring is selected from the group consisting of thiazolyl, isothiazolyl, pyrazolyl and imidazolyl.

85. The method of treatment of claim 79, wherein the 5-membered heterocycic ring contains 3 heteroatoms and each of said 3 heteroatoms is independently selected from the group consisting of O, N and S.

86. The method of treatment of claim 79, wherein the heterocycle of the 5-membered heterocyclic ring is thiadiazolyl.

87. The method of treatment of claim 79, wherein the 5-membered heterocyclic ring is substituted with one or more substituents selected from the group consisting of $C_{1-6}$alkyl and halogen.

88. The method of treatment of claim 75, wherein $R_3$ is methyl.

89. The method of treatment of claim 75, wherein $R_4$ and $R_5$ are the same or different and each represents hydrogen, fluorine or chlorine.

90. The method of treatment of claim 75, wherein $R_4$ and $R_5$ are the same or different and each represents hydrogen or fluorine.

91. The method of treatment of claim 75, wherein both $R_4$ and $R_5$ are fluorine.

92. The method of treatment of claim 75, wherein $R_1$ is fluoromethyl; $R_2$ is —C(=O)-2-furanyl; $R_3$ is methyl; $R_4$ and $R_5$ are the same or different and each represents hydrogen or fluorine; and === represents a single or a double bond.

93. The method of treatment of claim 75, wherein === represents a double bond.

94. The method of treatment of claim 75, wherein the method is for veterinary medicine.

95. The method of treatment of claim 75, wherein the method is for human medicine.

96. The method of treatment of claim 75, wherein the pharmaceutical composition is in admixture with one or more physiologically acceptable diluents or carriers.

97. The method of treatment of claim 75, wherein the pharmaceutical formulation further comprises a fluorocarbon or hydrogen-containing chlorofluoro carbon as propellant, optionally in combination with a surfactant and/or a cosolvent.

98. The method of treatment of claim 96, wherein the composition is a dry powder or spray.

99. The method of treatment of claim 98, wherein the composition is a dry powder.

100. The method of treatment of claim 98, wherein the composition is a spray.

101. The method of treatment of claim 75, wherein the $\beta_2$-adrenoreceptor agonist is at least one selected from the group consisting of salmeterol, salbutamol, formoterol, salmefamol, fenoterol, terbutaline and salts thereof.

102. The method of treatment of claim 75, wherein said compound of formula (I) has a particle size in the range of 1–10 μm.

103. The method of treatment of claim 75, wherein the compound of formula (I) or a solvate thereof and the long-acting $\beta_2$-adrenoreceptor agonist are both present in particulate form.

104. The method of treatment of claim 103, wherein said pharmaceutical formulation further comprising a particulate carrier.

105. The method of treatment of claim 104, wherein the carrier in said pharmaceutical formulation is lactose.

106. The method of treatment of claim 75, wherein said pharmaceutical formulation further comprises a liquified propellant gas.

107. The method of treatment of claim 103, wherein said, pharmaceutical formulation further comprises a liquified propellant gas.

108. The method of treatment of claim 1, wherein the compound of formula (I) is 6α,9α-Difluoro-17α-[(2-furanylcarbonyl)oxy]-11β-hydroxy-16α-methyl-3-oxo-androsta-1,4-diene-17β-carbothioic acid S-fluoromethyl ester or a salt or solvate thereof.

109. The method of treatment of claim 108, wherein the compound or salt or solvate thereof is together, if desirable, in admixture with one or more physiologically acceptable diluents or carriers.

110. The method of treatment of claim 108, wherein the pharmaceutical formulation further comprises a fluorocarbon or hydrogen-containing chlorofluoro carbon as propellant, optionally in combination with a surfactant and/or a cosolvent.

111. The method of treatment of claim 108, wherein the pharmaceutical formulation is a dry powder or spray.

112. The method of treatment of claim 111, wherein the composition is a dry powder.

113. The method of treatment of claim 111, wherein the composition is a spray.

114. The method of treatment of claim 108, wherein the $\beta_2$-adrenoreceptor agonist is at least one selected from the group consisting of salmeterol, salbutamol, formoterol, salmefamol, fenoterol, terbutaline and salts thereof.

115. The method of treatment of claim 108, wherein said compound of formula (I) has a particle size in the range of 1–10 μm.

116. The method of treatment of claim 108, wherein the method is for veterinary medicine.

117. The method of treatment of claim 108, wherein the method is for human medicine.

118. The method of treatment of claim 108, wherein the compound of formula (I) or a solvate thereof and the long-acting $\beta_2$-adrenoreceptor agonist are both present in particulate form.

119. The method of treatment of claim 118, wherein said pharmaceutical formulation further comprising a particulate carrier.

120. The method of treatment of claim 119, wherein the carrier in said pharmaceutical formulation is lactose.

121. The method of treatment of claim 108, wherein said pharmaceutical formulation further comprises a liquified propellant gas.

122. The method of treatment of claim 118, wherein said pharmaceutical formulation further comprises a liquified propellant gas.

123. The method of treatment of claim 14, wherein the compound or salt or solvate thereof is together, if desirable, in admixture with one or more physiologically acceptable diluents or carriers.

124. The method of treatment of claim 14, wherein the pharmaceutical formulation further comprises a fluorocarbon or hydrogen-containing chlorofluoro carbon as propellant, optionally in combination with a surfactant and/or a cosolvent.

125. The method of treatment of claim 14, wherein the pharmaceutical formulation is a dry powder or spray.

126. The method of treatment of claim 125, wherein the pharmaceutical formulation is a dry powder.

127. The method of treatment of claim 125, wherein the composition is a spray.

128. The method of treatment of claim 14, wherein the $\beta_2$-adrenoreceptor agonist is at least one selected from the group consisting of salmeterol, salbutamol, formoterol, salmefamol, fenoterol, terbutaline and salts thereof.

129. The method of treatment of claim 14, wherein said compound of formula (I) has a particle size in the range of 1–10 μm.

130. The method of treatment of claim 14, wherein the method is for veterinary medicine.

131. The method of treatment of claim 14, wherein the method is for human medicine.

132. The method of treatment of claim 14, wherein the compound of formula (I) or a solvate thereof and the long-acting $\beta_2$-adrenoreceptor agonist are both present in particulate form.

133. The method of treatment of claim 132, wherein said pharmaceutical formulation further comprising a particulate carrier.

134. The method of treatment of claim 133, wherein the carrier in said pharmaceutical formulation is lactose.

135. The method of treatment of claim 14, wherein said pharmaceutical formulation further comprises a liquified propellant gas.

136. The method of treatment of claim 132, wherein said pharmaceutical formulation further comprises a liquified propellant gas.

137. The method of treatment of claim 14, wherein the compound or salt or solvate thereof is together, if desirable, in admixture with one or more physiologically acceptable diluents or carriers.

138. The method of treatment of claim 14, wherein the pharmaceutical formulation further comprises a fluorocarbon or hydrogen-containing chlorofluoro carbon as propellant, optionally in combination with a surfactant and/or a cosolvent.

139. The method of treatment of claim 14, wherein the pharmaceutical formulation is a dry powder or spray.

140. The method of treatment of claim 139, wherein the pharmaceutical formulation is a dry powder.

141. The method of treatment of claim 139, wherein the composition is a spray.

* * * * *